US010856775B2

(12) United States Patent
Ribble et al.

(10) Patent No.: US 10,856,775 B2
(45) Date of Patent: Dec. 8, 2020

(54) METHOD OF PREDICTING OCCUPANT EGRESS FROM AN OCCUPANT SUPPORT BASED ON PERIMETER PANEL STATUS AND OCCUPANT LOCATION, AND A RELATED APPARATUS

(71) Applicant: Hill-Rom Services, Inc., Batesville, IN (US)

(72) Inventors: David L. Ribble, Indianapolis, IN (US); Yongji Fu, Harrison, OH (US); Kirsten M. Emmons, Batesville, IN (US)

(73) Assignee: Hill-Rom Services, Inc., Batesville, IN (US)

(*) Notice: Subject to any disclaimer, the term of this patent is extended or adjusted under 35 U.S.C. 154(b) by 549 days.

(21) Appl. No.: 15/000,258

(22) Filed: Jan. 19, 2016

(65) Prior Publication Data
US 2017/0156638 A1 Jun. 8, 2017

Related U.S. Application Data

(60) Provisional application No. 62/263,991, filed on Dec. 7, 2015.

(51) Int. Cl.
*A61B 5/11* (2006.01)
*A61G 7/012* (2006.01)
(Continued)

(52) U.S. Cl.
CPC .......... *A61B 5/1115* (2013.01); *A61B 5/6892* (2013.01); *A61B 5/7275* (2013.01); *A61G 7/005* (2013.01); *A61G 7/012* (2013.01); *A61G 7/015* (2013.01); *A61G 7/018* (2013.01); *A61G 7/0507* (2013.01); *A61G 2007/052* (2013.01); *A61G 2007/0516* (2013.01);
(Continued)

(58) Field of Classification Search
CPC ........ A61G 7/005; A61G 7/012; A61G 7/015; A61G 7/018; A61G 7/0507; A61B 5/1115; A61B 5/6892; A61B 5/7275
USPC ........................................................ 600/595
See application file for complete search history.

(56) References Cited

U.S. PATENT DOCUMENTS 6,208,250 B1  3/2001  Dixon et al.
7,538,659 B2  5/2009  Ulrich et al.
(Continued)

FOREIGN PATENT DOCUMENTS

WO       2009064788 A1   5/2009
WO       2012040554 A2   3/2012
WO    WO 2012/040554 A2  3/2012

*Primary Examiner* — Daniel L Cerioni
(74) *Attorney, Agent, or Firm* — Kenneth C. Baran

(57) ABSTRACT

A method of evaluating the likelihood that an occupant will exit an occupant support comprises determining if the location of the occupant on the occupant support is displaced relative to a reference location, and if the location of the occupant is so displaced, designating that the occupant is at a risk of exiting the occupant support which is elevated relative to the baseline risk. A support apparatus comprises a framework, a mattress, sensors distributed on the support apparatus to sense occupant weight distribution on the support apparatus, and a processor adapted to designate a risk of occupant egress as a function of the direction of the occupant weight distribution and the elevation status of the perimeter panels.

1 Claim, 17 Drawing Sheets

(51) Int. Cl.
*A61G 7/015* (2006.01)
*A61G 7/018* (2006.01)
*A61G 7/005* (2006.01)
*A61G 7/05* (2006.01)
*A61B 5/00* (2006.01)

(52) U.S. Cl.
CPC ............ *A61G 2007/0519* (2013.01); *A61G 2007/0527* (2013.01); *A61G 2203/44* (2013.01); *A61G 2203/70* (2013.01)

(56) References Cited

U.S. PATENT DOCUMENTS

| | | |
|---|---|---|
| 9,041,810 B2 | 5/2015 | Ecker et al. |
| 2007/0132597 A1 | 6/2007 | Rodgers |
| 2007/0157385 A1* | 7/2007 | Lemire .................. A61G 7/005 5/600 |
| 2007/0174965 A1* | 8/2007 | Lemire .................. A61G 7/005 5/600 |
| 2008/0021731 A1* | 1/2008 | Rodgers ................ A61B 5/1113 705/2 |
| 2012/0029879 A1 | 2/2012 | Sing et al. |
| 2012/0089419 A1* | 4/2012 | Huster .................. A61B 5/1115 705/3 |
| 2013/0246088 A1 | 9/2013 | Huster et al. |
| 2013/0276237 A1* | 10/2013 | Bobey ................ A61G 7/05776 5/658 |
| 2014/0022081 A1* | 1/2014 | Ribble .................. A61B 5/746 340/573.4 |
| 2014/0259410 A1* | 9/2014 | Zerhusen ................ A61G 7/00 5/600 |
| 2014/0345060 A1* | 11/2014 | Ribble .................. A61G 7/015 5/706 |
| 2016/0128610 A1* | 5/2016 | Kostic .................. A61B 5/1115 5/613 |

* cited by examiner

METHOD OF PREDICTING OCCUPANT EGRESS FROM AN OCCUPANT SUPPORT BASED ON PERIMETER PANEL STATUS AND OCCUPANT LOCATION, AND A RELATED APPARATUS

BACKGROUND

Occupant supports, such as beds used in hospitals, other health care facilities and home health care settings may be equipped with an exit assessment system. A typical exit assessment system uses sensed parameters and an algorithm to assess whether an occupant of the occupant support is attempting to exit the occupant support and, if so, provide a warning to a nearby caregiver. The sensed parameters are those that might indicate a change in the occupant's position which is consistent with an attempt to exit the bed. However existing exit systems do not take advantage of other potentially relevant and readily available information such as information about the occupant and information about the state of the bed itself, the status of certain of its components, and the local environment.

SUMMARY

A method of evaluating the likelihood that an occupant will exit an occupant support comprises determining if the location of the occupant on the occupant support is displaced in a direction toward a perimeter panel having an elevation status of DOWN and, if so, designating that the occupant is at a risk of exiting the occupant support which is elevated relative to a baseline risk associated with a reference location.

A support apparatus which carries out the method comprises a framework having perimeter panels, sensors distributed on the support apparatus to sense occupant weight distribution on the support apparatus, and a processor adapted to determine a direction of the occupant weight distribution relative to a reference weight distribution and to designate a risk of occupant egress as a function of the occupant weight distribution and the elevation status of the perimeter panels.

BRIEF DESCRIPTION OF THE DRAWINGS

The foregoing and other features of the various embodiments of a support apparatus and a method for evaluating the likelihood that an occupant of an occupant support will exit the occupant support will become more apparent from the following detailed description and the accompanying drawings in which.

DETAILED DESCRIPTION

Figure 1:
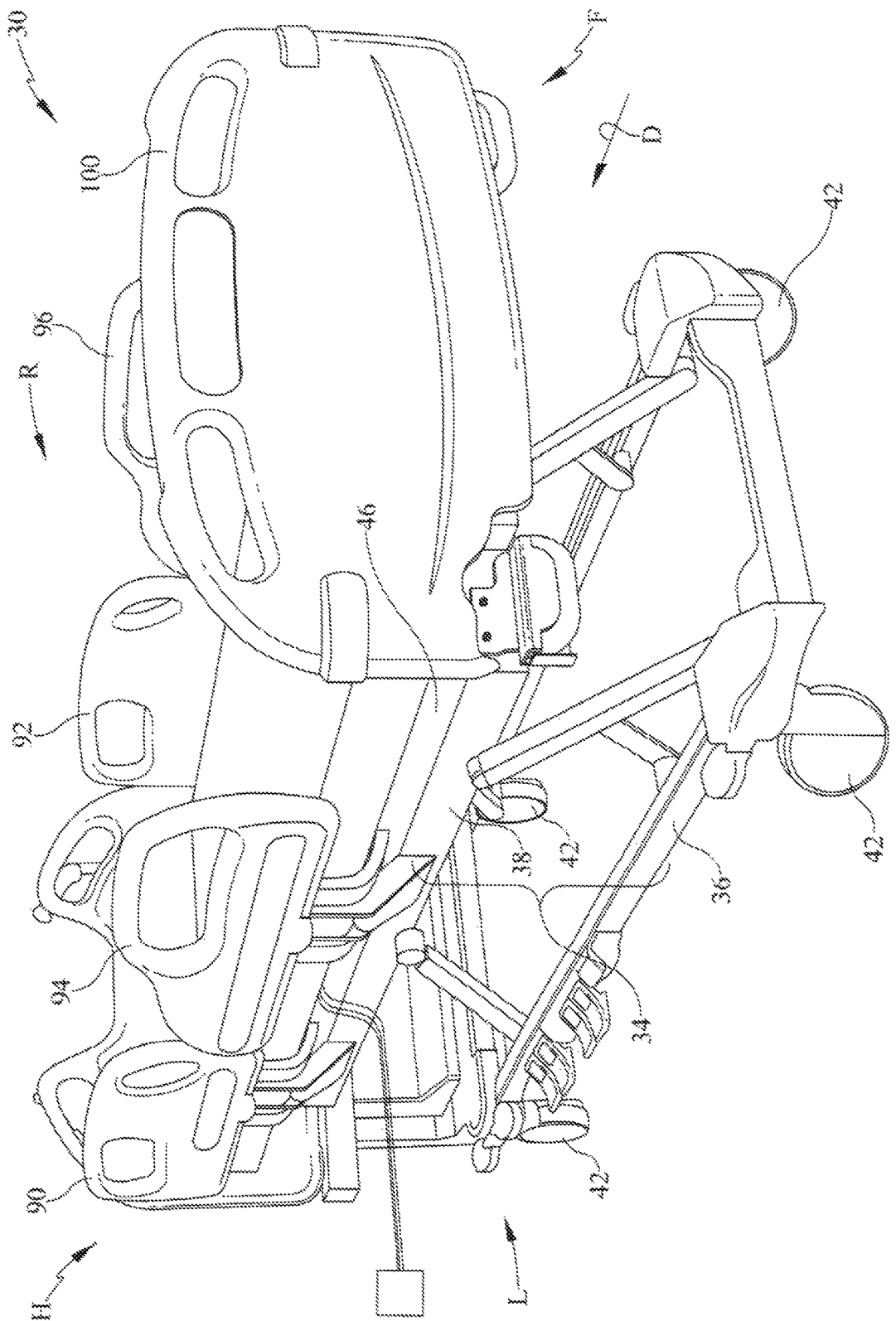
FIG. 1 is a perspective view of an occupant support exemplified as a typical hospital bed.
Figure 2:
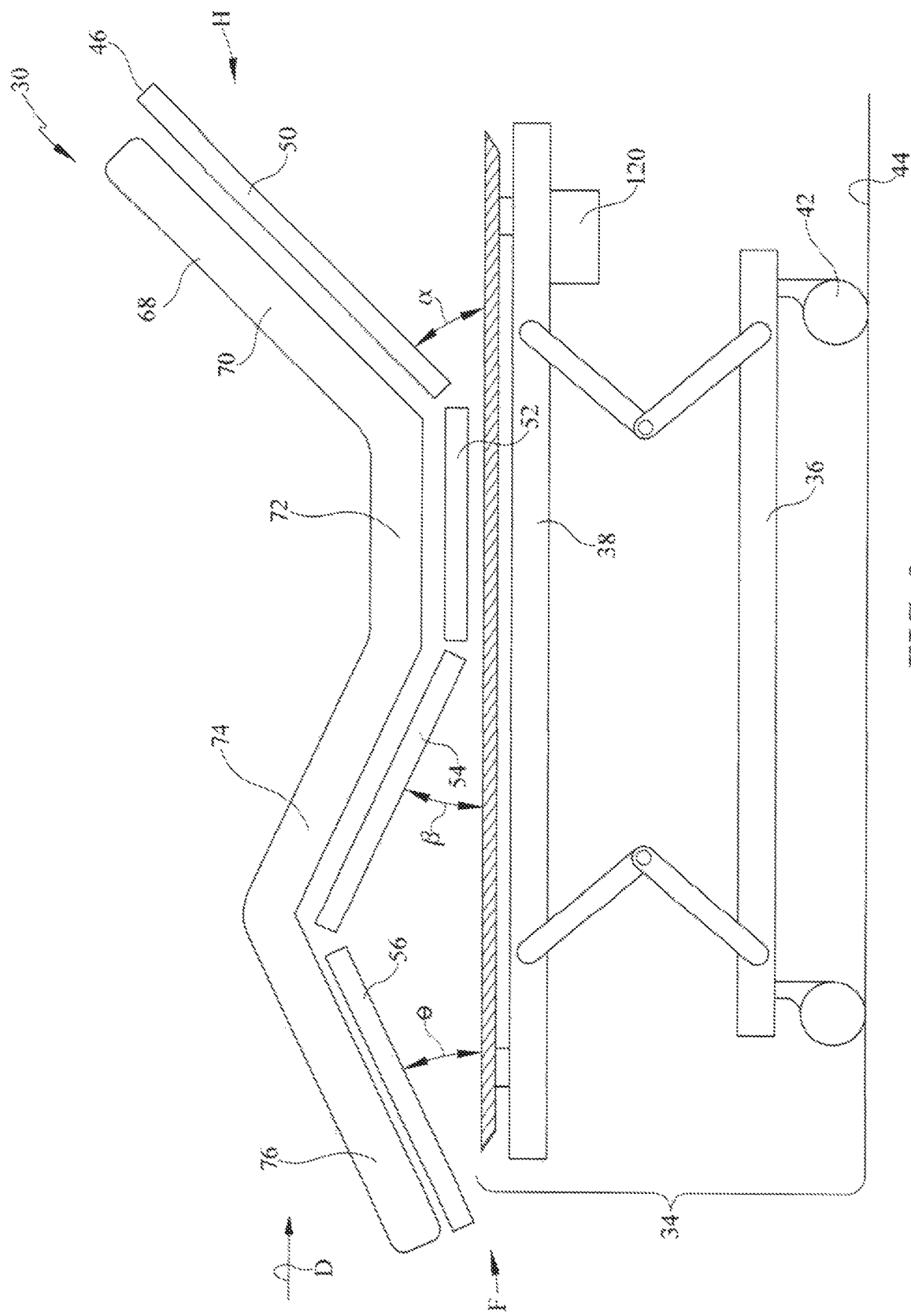
FIG. 2 is a side elevation view of a hospital bed similar to that of FIG. 1.

FIGS. 1-2 illustrate a bed 30 of the type used in hospitals, other health care facilities and home care environments. Bed 30 includes a framework 34 comprised of a base frame 36 and an elevatable frame 38 which is vertically moveable relative to the base frame as indicated by directional arrow V. The bed extends longitudinally from a head end H to a foot end F and laterally from a left side L to a right side R, where left and right are taken from the perspective of an observer at the foot end of the bed looking headwardly, i.e. in direction D of FIGS. 1 and 2. Framework 34 includes casters 42 extending from the base frame to floor 44. The elevatable frame 38 includes a deck generally indicated by 46. The deck is a segmented deck which includes an upper body or torso section 50 corresponding approximately to a supine occupant's torso, a seat section 52 corresponding approximately to the occupant's buttocks, a thigh section 54 corresponding approximately to the occupant's thighs and a calf section 56 corresponding approximately to the occupant's calves and feet.

Figure 3:
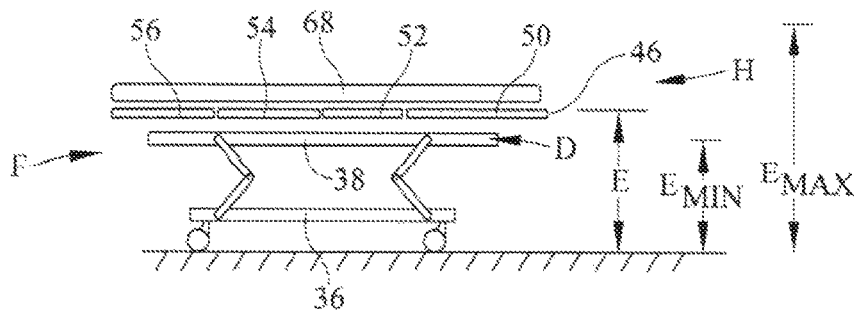
FIGS. 3-8 are schematic side elevation views illustrating elevation, inclination, and profile adjustability of a hospital bed such as those of FIGS. 1 and 2.
Figure 4:
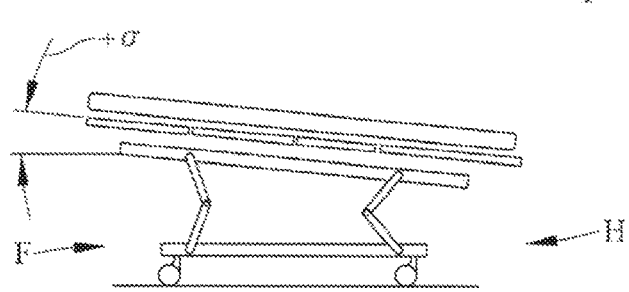
Figure 5:
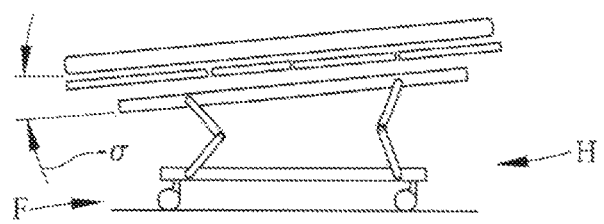
Figure 6:
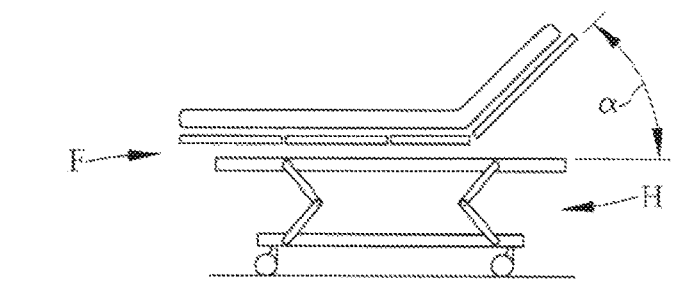
Figure 7:
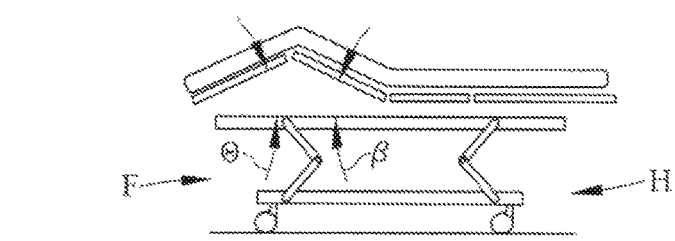
Figure 8:
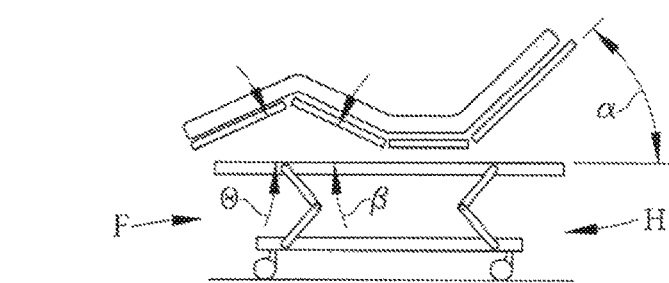

Referring additionally to FIGS. 3-8, the bed includes actuators, not illustrated, to adjust its elevation, inclination and profile. FIG. 3 shows adjustability of elevation E from a minimum elevation $E_{MIN}$ to a maximum elevation $E_{MAX}$. Elevation E is taken to be the elevation, relative to floor 44, of reference datum D on the elevatable frame. FIGS. 4-5 show adjustability of orientation angle σ to positive values +σ at which the head end of the elevatable frame is lower than the foot end and to negative values −σ at which the head end of the elevatable frame is higher than the foot end. FIGS. 2 and 6-8 show profile adjustability of the bed, specifically of the upper body, thigh and calf deck sections. Upper body section 50 is orientation adjustable relative to elevatable frame 38 through an angle α. The thigh and calf sections are orientation adjustable relative to the elevatable frame through angles β, θ. Typically angles β, θ are interdependent rather than independently selectable.

Bed 30 also includes a mattress 68. The mattress, unlike deck 46 is not segmented, but, like the deck, can be thought of as having an upper body or torso section 70, a seat section 72, a thigh section 74 and a calf section 76, each corresponding approximately to the occupant's torso, buttocks, thighs and calves and therefore corresponding to the similarly named deck sections. The mattress rests on the deck section of the elevatable frame and is affixed to the elevatable frame in any suitable manner such that mattress upper body section, thigh section and calf section change angular orientation in concert with changes in the angular orientation of the corresponding frame sections. Accordingly, the symbols α, β, θ may be used when necessary to indicate the angular orientations of the mattress sections as well as the orientations of the deck sections.

The bed also includes a set of perimeter panels shown only in FIG. 1. The perimeter panels include an upper left siderail 90, an upper right siderail 92, a lower left siderail 94, a lower right siderail 96, and a footboard 100. As used herein, "panel", "-rail", and "-board" are not intended to imply that the components referred to are of any particular form or construction. In addition, "upper" and "lower" are used to identify siderails that are closer to the head end H and foot end F respectively of the bed. The four siderail design is typical of beds manufactured for the United States market. In other markets beds with only two siderails, one left and one right, may be more typical. The examples used in this application are based on the four siderail design, however the principles described herein are applicable to n-siderail designs including n=2.

The siderails are elevatable and de-elevatable between a deployed elevation or position (FIG. 1) and a stowed elevation or position (not illustrated). The deployed position is a position in which the siderail is at its maximum elevation. The maximum elevation is an elevation at which, when the thickest mattress that the framework is intended to accommodate is installed on the framework, the top of the siderail is higher than the top of the mattress and is high enough to discourage occupant egress from the bed. In addition, when the siderail is at its deployed position, the siderail is rendered immovable or immobilized by an immobilizer so that it cannot be moved from that position without some intentional action on the part of a user (e.g. a caregiver) to overcome the immobilizing effect of the immobilizer. Typically the immobilizer is a latching mechanism which imparts the immovability or immobilization to the siderail; the user must intentionally release the latch in order to move the siderail from its maximum elevation. Because the siderail cannot be moved without some intentional action by a user to defeat the immobilizer, the deployed position may be thought of as a stable position.

The stowed position is one at which the top of the siderail is at a lower elevation than the maximum elevation. More typically the stowed position is a position at which when the least thick mattress that the framework is intended to accommodate is installed on the frame, the top of the siderail is lower than the top of the mattress. Even more typically the stowed position is one at which the top of the sidrerail is lower than the deck. The stowed position is a position suitable for occupant egress. On most beds there is no latch or other device to immobilize the siderail when the siderail is stowed, and therefore the stowed position can often be distinguished from the deployed position (and from intermediate positions described below) not only by the elevation of the siderail but also by the absence of immobilization. Even if an immobilizer is present and is used to immobilize the siderail in its stowed position, the stowed position is typically the lowest position or most "out of the way" position that the siderail can attain.

Some siderails may also be stably positionable at one or more intermediate position or elevation by the action of an immobilizer. The intermediate elevation is lower than the deployed elevation and higher than the stowed elevation.

Each siderail can be thought of as having an elevation status of either UP or DOWN. As used herein, UP refers to the stable, deployed position of a siderail. DOWN refers to the stowed position of the siderail. An intermediate position may be assigned a status of either UP or DOWN depending on the designer's assessment of the extent to which the elevation of the siderail discourages or accommodates occupant egress. For example an intermediate position in which the top of the siderail is below its maximum elevation but still considerably above the top of the thickest mattress will most likely be assigned a status of UP. An intermediate position in which the top of the siderail is above its stowed elevation but still considerably below the top of the least thick mattress will most likely be assigned a status of DOWN. Intermediate positions in which the top of the siderail is only slightly above the top of the thickest mattress or only slightly below the bottom of the least thick mattress are more subject to designer discretion in assigning an UP or DOWN status to the siderail elevation. This is because a siderail that projects only slightly above a mattress may not be judged to be effective for discouraging egress of a determined occupant. That intermediate siderail elevation might therefore be assigned a status of DOWN. Conversely a siderail whose top is only slightly below the top of the mattress might be judged to be effective at deterring occupant egress because the occupant's weight will compress the edge of the mattress as she attempts to egress, causing her legs to contact the top of the siderail. Such contact may serve as a deterrent to egress, especially if the occupant is not highly motivated. That intermediate siderail elevation might therefore be assigned a status of UP. Of course, any siderail elevation higher than an elevation defined as UP is also an UP elevation and any siderail elevation lower than an elevation defined as DOWN is also a DOWN elevation.

In the case of a siderail which is positionable only at its deployed and stowed positions (and not at any intermediate positions) and in which a latch is engaged only at the deployed position, elevation status of UP or DOWN may be established by a sensor which senses latch engagement.

Once a status of UP or DOWN is assigned to an intermediate siderail position for a given framework and model or class of mattress, that status is a fixed attribute for the egress evaluation methods and systems described herein. In other words the UP or DOWN status of a given intermediate siderail elevation is not affected by the methods or systems for evaluating egress risk. However the UP or DOWN status of a particular intermediate siderail position can be made field adjustable to better accommodate different models or classes of mattresses that are compatible with the bed framework. The adjustability could be accomplished by, for example, a user input to a controller or by an automated input to the controller, such as a return signal from an RFID tag on the mattress. Nevertheless, the status assigned to a given intermediate elevation is a fixed attribute of the framework/mattress combination, not a parameter which is affected by the egress risk evaluation methods or systems described herein. In the interest of explanatory simplicity, the examples in this application consider only a deployed (UP) siderail and a stowed (DOWN) siderail.

As already noted the perimeter panels include footboard 100 at the foot end of the bed. The footboard, unlike the siderails, is not usually elevatable and de-elevatable, however on some beds the footboard is removable and installable by a user such as a caregiver. A removable footboard can be thought of as having an assigned status of UP or DOWN. The UP status corresponds to the footboard being installed at the foot of the bed; the DOWN status corresponds to the footboard having been removed from the foot of the bed. A footboard which is not removable has an assigned status of UP or is not considered in the egress risk evaluation method.

Figure 9:
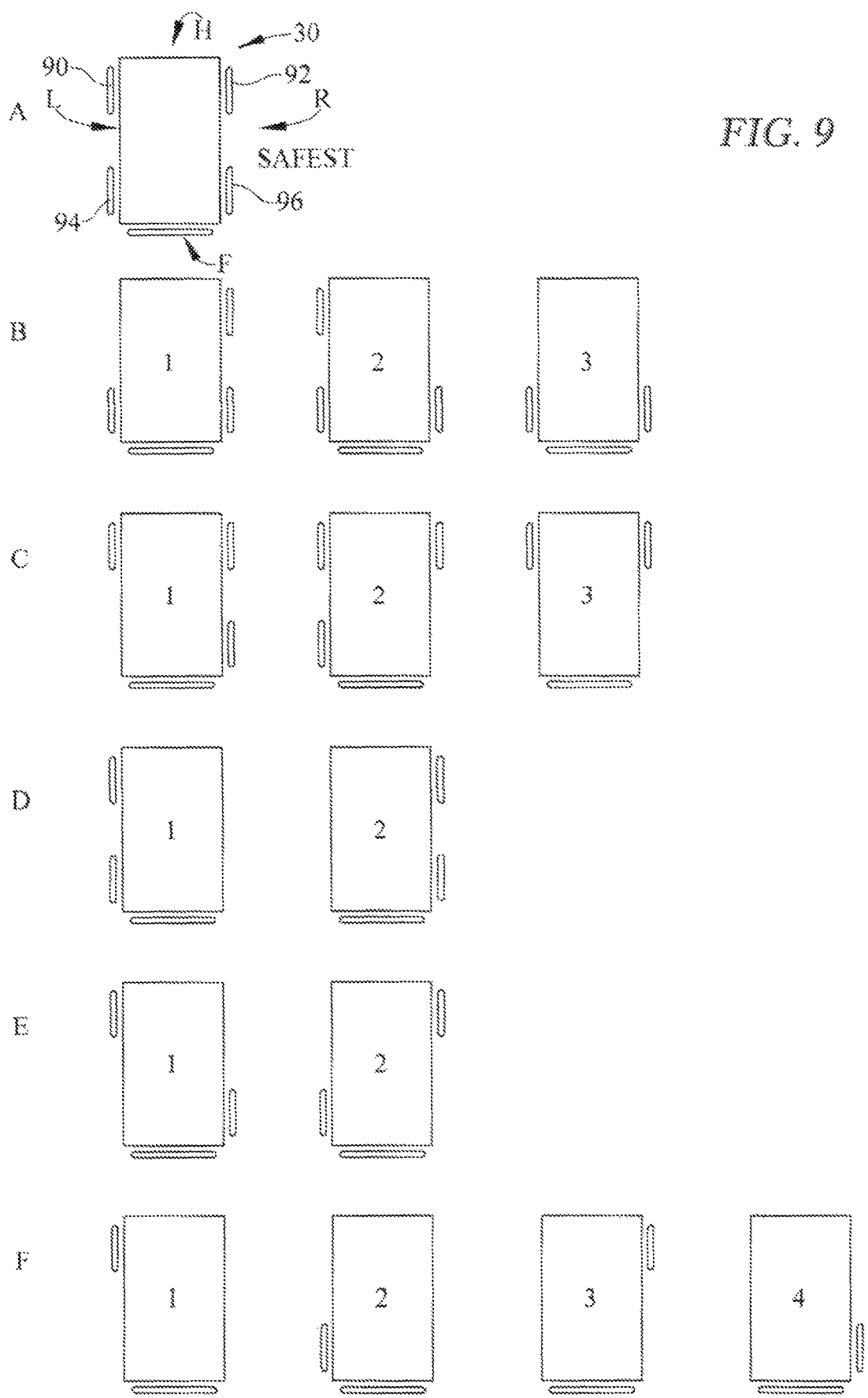
FIG. 9 is a set of schematic plan views illustrating fifteen of sixteen possible siderail configurations for a four-siderail bed.

FIG. 9 is a set of schematic plan views illustrating fifteen of sixteen possible siderail configurations for a four-siderail bed. The sixteenth configuration, all siderails DOWN, is not illustrated. As used herein, "siderail configuration" means one of the possible combinations of siderail status (UP, DOWN) that can be attained. (For a bed with n deployable and stowable siderails there are $2^n$ such combinations.) The schematic which illustrates the "all siderails UP" configuration includes reference characters H, F, L, and R to indicate the head end, foot end, left side and right side of the bed and reference numerals 90, 92, 94 and 96 to indicate the upper left, upper right, lower left, and lower right siderails. The other schematics of FIG. 9 are oriented the same way. Each siderail configuration is also identified by a code comprised of at least a letter (at the left side of the illustration sheet) and, if necessary, a number (shown in the planform of the bed).

Figure 10:
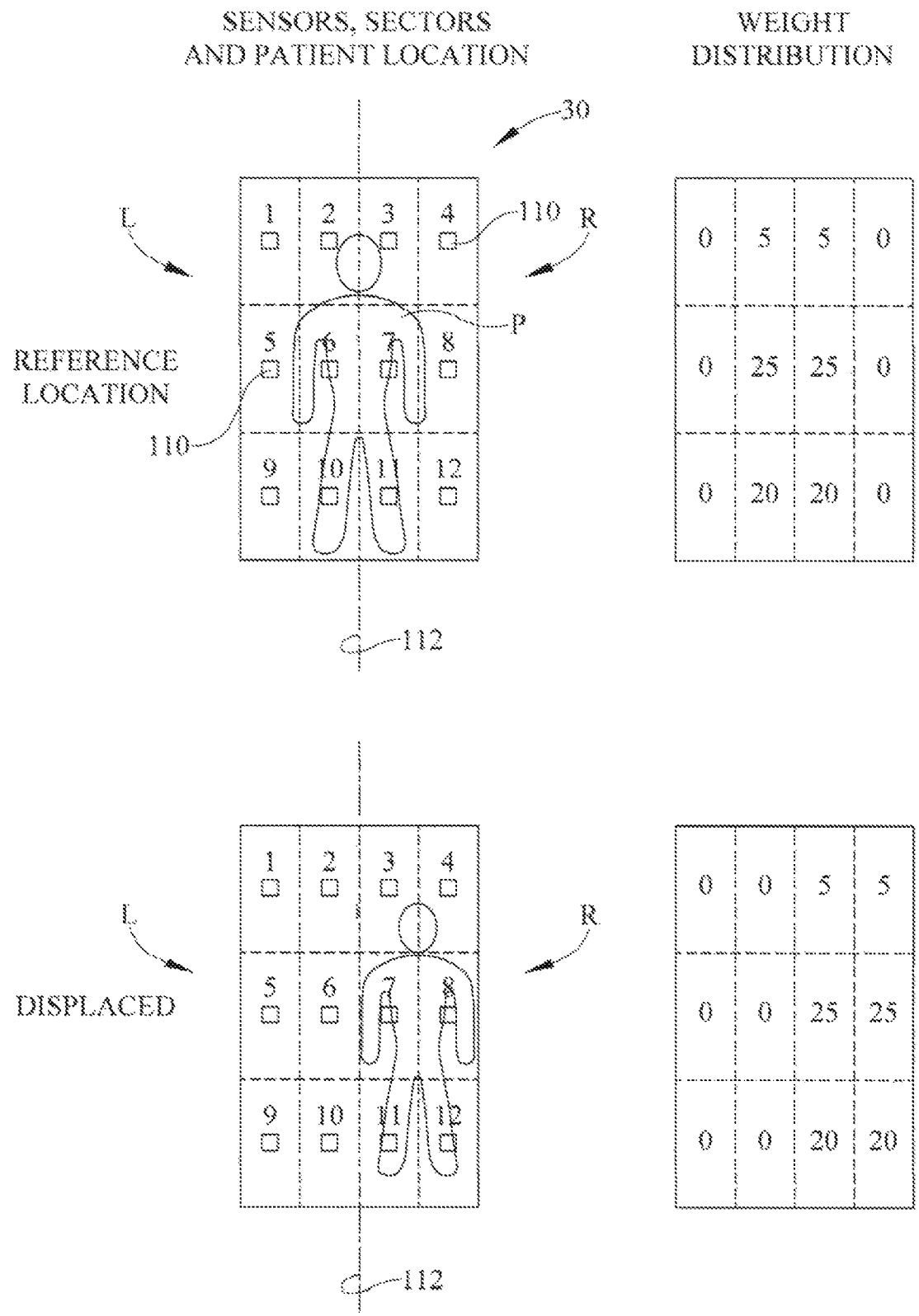
FIG. 10 is a set of plan views similar to those of FIG. 9, showing an example of the bed having been notionally divided into sectors forming a three row by four column grid and also showing one weight sensor per sector approximately centered in the sector. The schematics at the left show an occupant centered and offset to the right; the schematics at the left indicate the percentage weight distribution of the occupant in each of the sectors.

FIG. 10 is a set of plan views similar to those of FIG. 9, but showing an example of the bed having been notionally divided into sectors forming a three row by four column grid. The sectors are numbered 1 through 12. The bed includes one or more sensors, such as weight sensors 110. FIG. 10 shows one weight sensor for each sector approximately centered in its sector. The sensors are provided in order to determine how the weight of an occupant P is distributed within the planform of the bed and therefore to estimate the location of the occupant with respect to a reference location and to estimate the direction that the occupant might be displaced from the reference location. For example, the schematic at the top right of the drawing sheet shows a prophetic example of the percentage weight distribution of the centered occupant—5% in each of sectors 2 and 3, 25% in each of sectors 6 and 7, 20% in each of sectors 10 and 11, and 0% in all other sectors. The schematics at the bottom of the drawing sheet show the occupant off-centered to the right and show the corresponding weight distribution. The location of the occupant with respect to a reference location may also be thought of as (or as an indicator of) a direction and magnitude of occupant displacement relative to the reference location.

Figure 11:
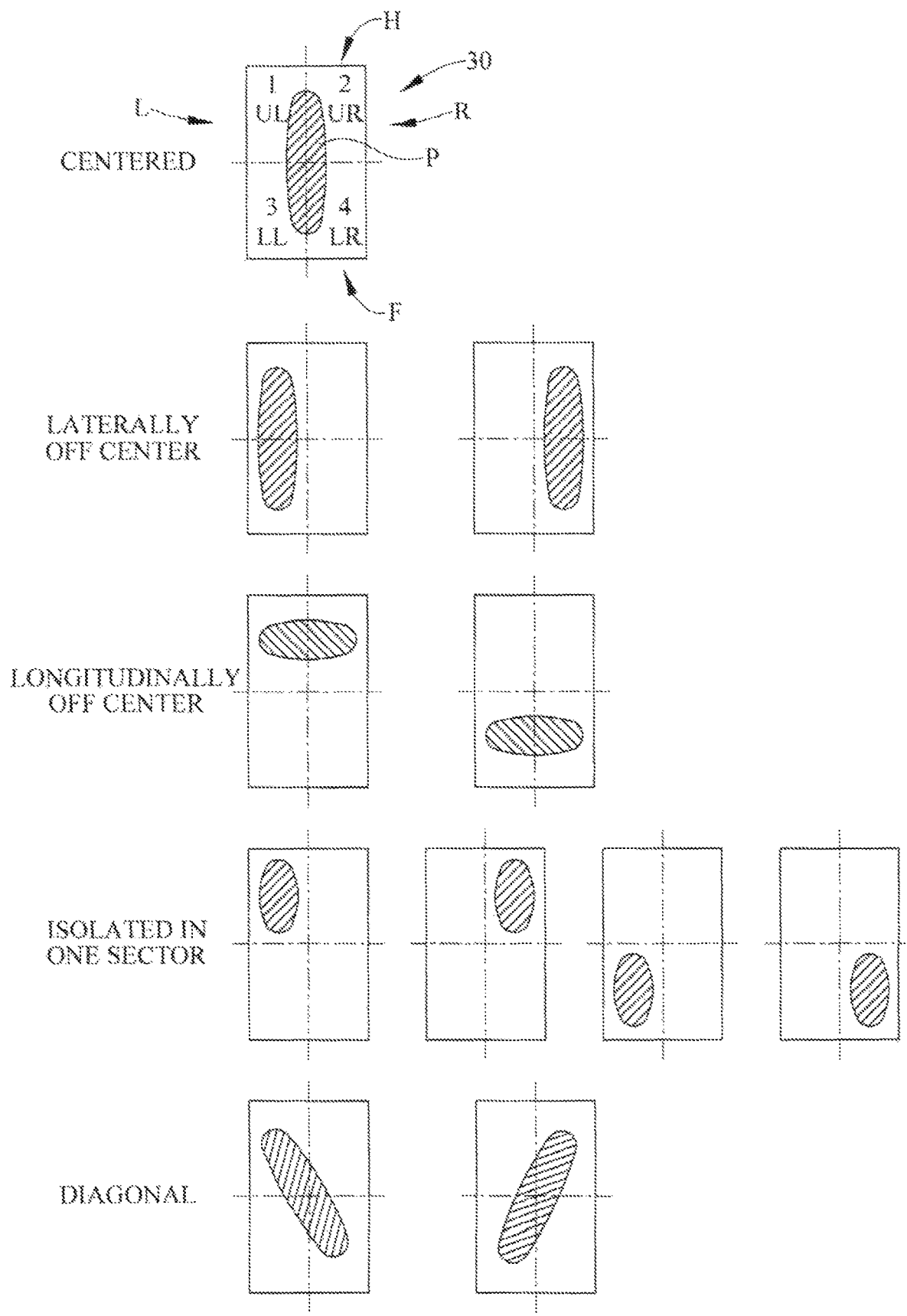
FIG. 11 is a set of plan views similar to those of FIG. 10, but showing an example of a bed having been notionally divided into four sectors and also showing a symbolically illustrated occupant P in different locations, including a diagonal location or orientation.

FIG. 11 is a set of plan views similar to those of FIG. 10, but showing an example of a bed having been notionally divided into four sectors labeled as UL, UR, LL, LR (upper left, upper right, lower left, lower right). The sectors are also numbered 1 through 4. The bed includes sensors, such as the sensors 110 already described, however the sensors are not illustrated in the interest of avoiding undue clutter on the illustration. FIG. 11 also includes a symbolically illustrated occupant P centered on the bed, laterally off center to the left, laterally off center to the right, longitudinally off center toward the head end H, longitudinally off center toward the foot end L, offset in four directions which are composites of the left, right, headward, and footward displacements, and offset diagonally, i.e. counterclockwise and clockwise.

Taking as an example the four sector occupant support of FIG. 11 with one weight sensor in each of the four sectors, and having four siderails as in FIG. 9, determining if the location of the occupant is displaced relative to the reference is as set forth in table A below in which, for each given sector, H signifies a higher than reference weight portion borne by that sector and L signifies a lower than reference weight portion borne by that sector, and wherein the column labelled "Occupant Displacement" indicates an interpretation of occupant displacement applied to the lower than reference and higher than reference weight portions in the same row.

TABLE A

| Sector Number | 1 | 2 | 3 | 4 | Occupant Displacement |
|---|---|---|---|---|---|
| Sector Location | UL | UR | LL | LR | |
| | NORMAL | NORMAL | NORMAL | NORMAL | Centered |
| | H | L | H | L | Displaced Left |
| | L | H | L | H | Displaced Right |
| | H | H | L | L | Displaced Headwardly |
| | L | L | H | H | Displaced Footwardly |
| Portion of Weight Relative to Reference | H | L | L | L | Displaced Headwardly and Left |
| | L | H | L | L | Displaced Headwardly and Right |
| | L | L | H | L | Displaced Footwardly and Left |
| | L | L | L | H | Displaced Footwardly and Right |
| | H | L | L | H | Displaced Counterclockwise |
| | L | H | H | L | Displaced Clockwise |

In the examples herein the reference location reflects the location of an occupant who is laterally and longitudinally centered as seen in the schematic at the top left of FIG. 10. However the reference location can be selected more arbitrarily if desired. The method as described herein includes accessing outputs from the weight sensors and comparing the outputs to a set of reference outputs. For example, due to the substantial left-right symmetry of the human body an occupant is laterally centered if, when lying supine on the bed, her saggital plane approximately coincides with bed longitudinal centerline 112. This would be indicated by, for example, approximately equal weight borne by sectors 2 and 3, approximately equal weight borne by sectors 6 and 7, and approximately equal weight borne by sectors 10 and 11 as seen in the percentage weight distribution schematics on the right side of the FIG. 10. A longitudinally centered occupant could be indicated if the longitudinal distribution of the occupant's weight conforms to a standard distribution, e.g. the 10%, 50%, 40% distribution seen in FIG. 10. In another embodiment the occupant is considered to be longitudinally centered if her anatomical features are correctly positioned relative to certain features of the bed. For example the occupant may be considered to be longitudinally centered if her buttocks is approximately longitudinally positioned over seat section 52 of the deck or if her hips are longitudinally aligned with a hip indicator on the bed.

As already noted sensors 110 are provided in order to determine how the weight of the occupant P is distributed within the planform of the bed and therefore to indicate the location of the occupant with respect to the reference location. The location of the occupant with respect to the reference location may also be thought of as (or as an indicator of) a direction and magnitude of occupant displacement relative to the reference location. Therefore, sensor arrangements other than the illustrated "one per sector/centered" arrangement may be satisfactory. Moreover the sensors may be components of framework 34 or components of mattress 68. In addition, other technologies capable of establishing occupant displacement relative to a reference may be employed. These include infrared sensing of occupant position and analysis of images in the visible spectrum.

Figure 12:
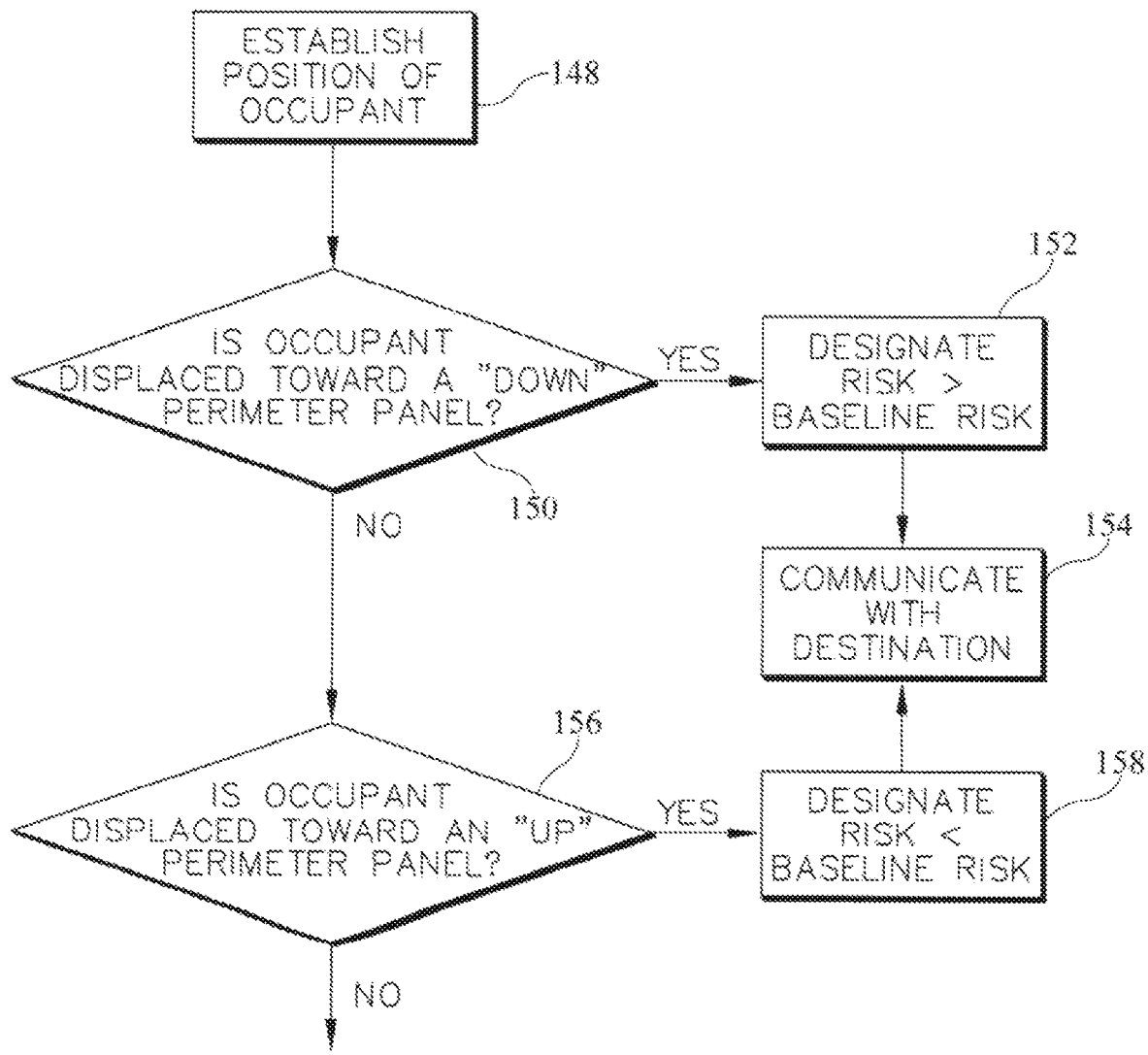
FIG. 12 is a block diagram showing a method of evaluating the likelihood or risk that an occupant of the occupant support will exit the occupant support, the risk being a function of occupant location on the occupant support and perimeter panel status.

FIG. 12 is a block diagram showing a method of evaluating the likelihood or risk that an occupant of the occupant support will exit the occupant support. The method of the block diagram is carried out by a processor 120 (FIG. 2) which is adapted to determine occupant weight distribution relative to a reference weight distribution and to designate a risk of occupant egress as a function of the occupant weight distribution and the elevation status of the perimeter panels. At block 150 the method determines if the location of the occupant on the occupant support, as revealed by the weight distribution of the occupant, is displaced, relative to a reference location, in a direction toward a perimeter panel having an elevation status of DOWN. If so, the method proceeds to block 152 and designates that the occupant is at a risk of exiting the bed which is elevated relative to a baseline risk associated with the occupant being located at the reference location (i.e. laterally and longitudinally centered). This is further illustrated with table 0 below. Table 0 shows the occupant displacements of FIG. 11. For each of those displacements the table also shows which perimeter panel or panels would have to have a status of DOWN in order for the occupant's risk of egress to be considered higher than the baseline risk. That is, the occupant is designated as being of elevated risk of exiting the bed only if occupant displacement and siderail status are both as set forth in one of the rows of table 0.

TABLE 0

| Occupant Displacement | Siderail(s) which have a status of "DOWN" |
|---|---|
| displaced left | One or both left siderails |
| displaced right | One or both right siderails |
| displaced headwardly | One or both upper siderails |

TABLE 0-continued

| Occupant Displacement | Siderail(s) which have a status of "DOWN" |
|---|---|
| displaced footwardly | One or both lower siderails |
| displaced headwardly and left | upper left siderail or both left siderails |
| displaced headwardly and right | upper right siderail or both right siderails |
| displaced footwardly and left | lower left siderail or both left siderails |
| displaced footwardly and right | lower right siderail or both right siderails |
| displaced counter-clockwise | upper left and lower right siderails |
| displaced clockwise | upper right and lower left siderails |

The diagram of FIG. 12 also shows that the step of determining if the location of the occupant is displaced, relative to a reference location, in a direction toward a perimeter panel having an elevation status of DOWN may be preceded by a step of establishing the location or position of the occupant on the occupant support (block 148). However such an explicit establishment of occupant location is not necessarily required because, at least in the case of the reference location corresponding to a centered occupant, knowledge that the occupant is displaced toward a DOWN perimeter panel (block 150) inherently establishes the position of the occupant, at least with enough sufficiency for the methods disclosed herein. The functions of FIG. 12 are carried out repetitively so that the method is responsive to changes in occupant position and perimeter panel status. One example update interval is 250 milliseconds.

The "NO" branch from block 150 may simply loop back to blocks 148, 150. However in the illustrated alternative the "NO" branch leads to block 156 which determines if the occupant is displaced in a direction toward an UP perimeter panel. If so, the method proceeds to block 158 where it designates that the occupant is at a risk of exiting the bed which is less than the baseline risk associated with the reference location. Alternatively block 158 may designate that the risk is nonelevated relative to the baseline risk associated with the reference location. Whether the risk is designated as "less than" or "nonelevated" is a matter of discretion exercised by the system designer.

As a practical matter, block 154 communicates the designation of risk to a destination. In one example the destination is a nurse's station and the communication takes the form of a message which need report nothing more than, for example, "ELEVATED EGRESS RISK—PATIENT D. RIBBLE". In another example the destination is a warning light near or on the bed, and the communication involves changing the state of the light from, for example OFF to ON or from green illumination to red illumination. The method as thus far disclosed therefore indicates an elevated or nonelevated risk relative to the baseline risk, but provides no information about the magnitude of the elevated or nonelevated risk.

In a variation of the method the step of designating that the occupant is at an elevated or nonelevated risk comprises graduating the risk, for example as LOW, MEDIUM, HIGH, or green, yellow, red, in order to provide information about the magnitude of the elevated risk.

Figure 13:
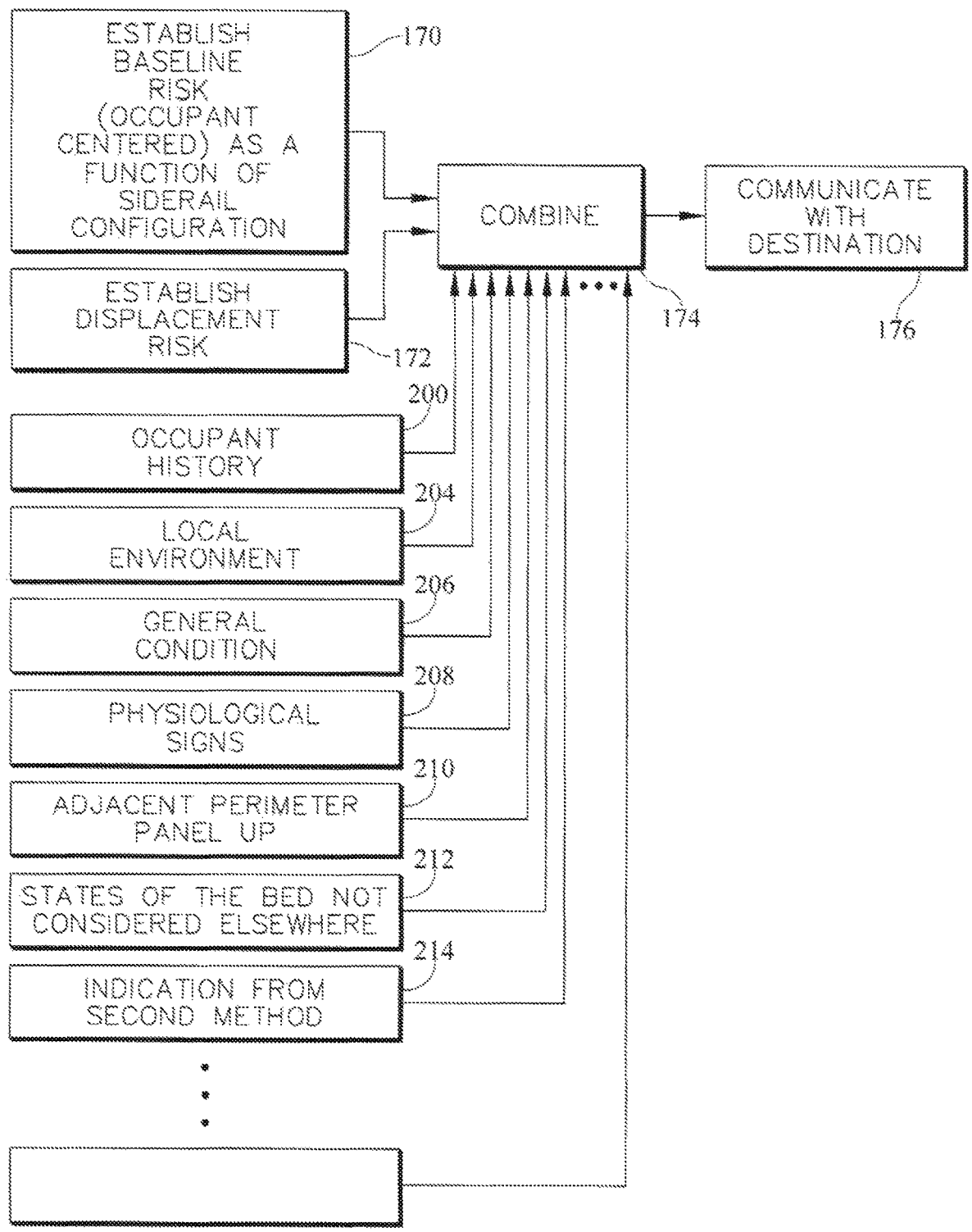
FIG. 13 is a block diagram showing additional risk contributors and provided in connection with quantifying the risk of occupant egress for a four siderail bed as in FIG. 9 notionally divided into four sectors as in FIG. 11.
Figure 14:
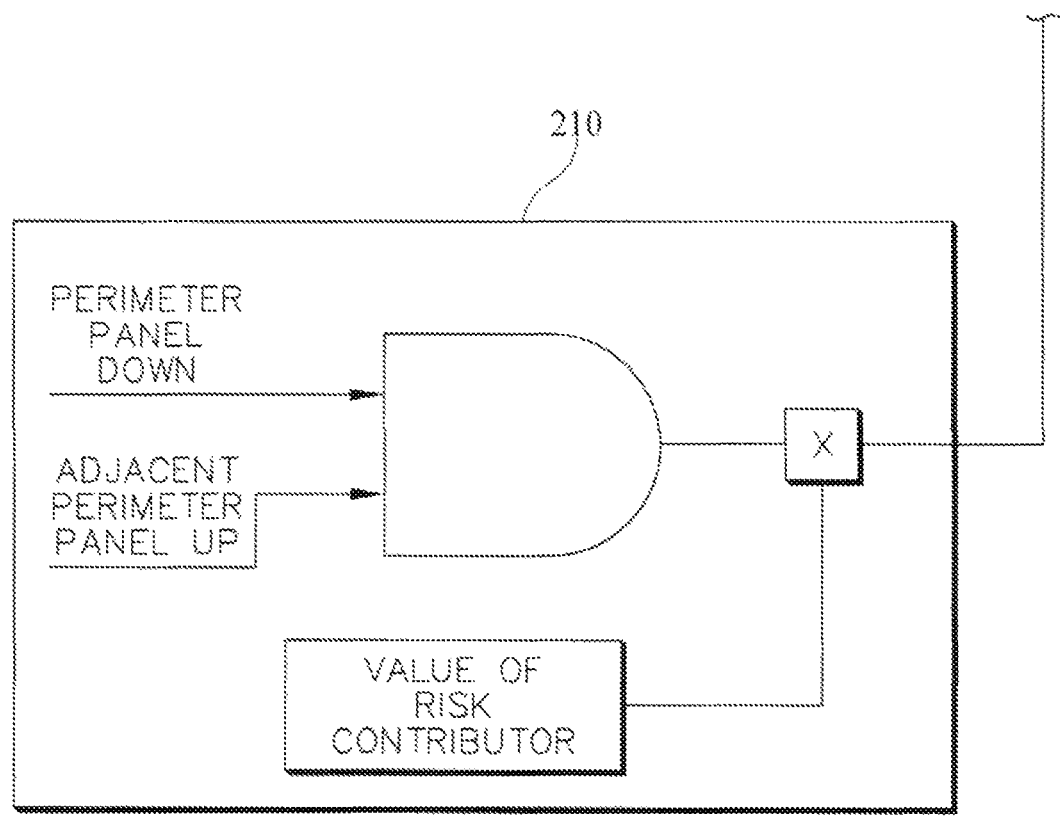
FIG. 14 is a logic diagram and truth table related to one of the additional risk contributors of FIG. 13.

Another way of graduating the risk is to quantify the risk. FIGS. 13-14 and Tables 1 and 2 below provide an example of quantifying the risk for a four siderail bed (FIG. 9) notionally divided into four sectors (FIG. 11) each having a weight sensor 110. Table 1 shows baseline risks, i.e. the egress risk for an occupant who is centered as indicated by the weight sensors. The table lists the sixteen possible siderail configurations of FIG. 9 (columns 1-4), the configuration identifier codes described in connection with FIG. 9 plus a code "G" for the case of all four siderails DOWN (column 5), and a quantified risk for a centered occupant associated with each siderail configuration (column 6). The numerical risk values are a prophetic example offered to make the concept more concrete. In the interest of simplicity, footboard status is not taken into account in the example of Table 1 (doing so would double the size of the table with no corresponding improvement in the explanatory power of the example).

TABLE 1

Baseline Risk (Centered Occupant)
Four Siderails
Four Sectors

| 1 | 2 | 3 | 4 | 5 | 6 |
|---|---|---|---|---|---|
| Perimeter Panel (Siderail) Configuration | | | | Config. Identifier | Quantified Risk |
| UL | UR | LL | LR | | |
| UP | UP | UP | UP | A | 0 |
| UP | UP | UP | DOWN | C2 | 20 |
| UP | UP | DOWN | UP | C1 | 20 |
| UP | UP | DOWN | DOWN | C3 | 20 |
| UP | DOWN | UP | UP | B2 | 10 |
| UP | DOWN | UP | DOWN | D1 | 25 |
| UP | DOWN | DOWN | UP | E1 | 20 |
| UP | DOWN | DOWN | DOWN | F1 | 30 |
| DOWN | UP | UP | UP | B1 | 10 |
| DOWN | UP | UP | DOWN | E2 | 20 |
| DOWN | UP | DOWN | UP | D2 | 25 |
| DOWN | UP | DOWN | DOWN | F3 | 30 |
| DOWN | DOWN | UP | UP | B3 | 10 |
| DOWN | DOWN | UP | DOWN | F2 | 30 |
| DOWN | DOWN | DOWN | UP | F4 | 30 |
| DOWN | DOWN | DOWN | DOWN | G | 30 |

A designer could assign a zero baseline risk to all sixteen configurations for the case of a centered occupant. However the example of Table 1, although representing a centered occupant, assigns a nonzero baseline risk to all the siderail configurations in which at least one siderail is DOWN. The nonzero baseline risks reflect the viewpoint that, even with the occupant centered, a siderail status of DOWN represents a nonzero risk. In determining the baseline risk associated with a given siderail configuration the designer may need to exercise some judgement. For siderail configurations B, the lower siderails are up and at least one upper siderail is down. The fact that the assigned risk when both upper siderails are DOWN is the same as the assigned risk when only one upper siderail is DOWN reflects a judgement that an occupant needs only one of the upper siderails to be DOWN to be at risk. Therefore, the fact that there are two exit paths, not just one, does not add to the risk when the occupant is centered.

In configurations C, the upper siderails are UP and at least one lower sidrerail is DOWN. The assigned risk is higher than it is with configuration B because it is more natural for the occupant to exit the bed in the vicinity of the lower siderails than in the vicinity of the upper siderails. The fact that the assigned risk when both lower siderails are DOWN is the same as the assigned risk when only one lower siderail is DOWN reflects a judgement that an occupant needs only one of the lower siderails to be DOWN to be at risk. Therefore, the fact that there are two exit paths, not just one, does not add to the risk when the occupant is centered.

In configurations D there are two siderails DOWN on the same side of the bed. The quantified risk reflects a judgement that two siderails DOWN on the same side of the bed leaves that side of the bed completely open and therefore is riskier than if only one siderail is down on that same side of the bed.

In configuration E, Two diagonally opposed siderails are UP, the other two are DOWN. The risk judgement is that this is no riskier than one or both lower rails being DOWN while both upper rails are UP.

In configuration F three siderails are DOWN, and therefore at least one of these must be a lower siderail which offers a more preferred exit path to the occupant than if an upper siderail were down. In addition, it is judged that both lower rails being DOWN down is no riskier than one lower rail being DOWN.

To further emphasize that the risk assignments of table 1 are subject to the designer's judgement, note that the D configurations might be judged to be less risky than the B and C configurations, rather than more risky as shown in table 1. Although the D configurations present the occupant with an unrestricted opportunity for exit on one entire side of the bed, there is nothing sturdy to help the occupant support herself during egress and immediately thereafter. By contrast, although configurations B and C offer less spatial opportunity for egress, the occupant can use an UP siderail for support.

Whether the baseline risk of Table 1 is considered to be zero or nonzero, the quantified baseline risk is adjusted, as appropriate, for occupant displacement as set forth in Table 2A and as described in the paragraphs following the table.

The displacements of columns 11-12 are referred to as diagonal displacements. They represent a change of occupant orientation in the counterclockwise sense (col. 11) or clockwise sense (col. 12) relative to the reference location/orientation. The system designer will, of course, apply appropriate tolerances to distinguish among the various displacements. For example in the four sector occupant support of FIG. 11 a 2% weight shift from a baseline distribution of:

UL=23%, UR=23%, LL=27%, LR=27%
to UL=25%, UR=21%, LL=29%, LR=25% may be not be considered to indicate any meaningful displacement of the occupant to the left whereas a 7% weight shift from the same baseline distribution to:

UL=30%, UR=16%, LL=34%, LR=20% may be considered to signify a definite leftward displacement.

The cells of table 2A include symbolic entries to reveal how each of the ten off-center occupant locations ("off center left" through "diagonal UR to LL") changes or adjusts the baseline risk of exit associated with each of the sixteen siderail configurations. An "I" or "I+" entry signifies an increased risk relative to the risk shown in table 1; a "D" entry signifies a decreased risk, and an "S" entry signifies that the risk stays the same. The cells of column 2, which correspond to the occupant centered (or zero displacement), are populated with "Baseline" but could have equivalently been populated with "S". In one example, if the siderail

TABLE 2A

Risk Adjustment Due to Occupant Displacement from Reference Location (Without Credit in the Composite Risks for Decreased Unidirectional Risk)

| 1 S/R Config | 2 Center | 3 Off center Left | 4 Off center Right | 5 off center Up | 6 Off center Down | 7 Up/ Left | 8 Up/ Right | 9 Low/ Left | 10 Low/ Right | 11 diag. UL to LR | 12 diag. UR to LL |
|---|---|---|---|---|---|---|---|---|---|---|---|
| | | Unidirectional | | | | Composite or Bidirectional | | | | Diagonal | |
| | | | | Weight Distribution | | | | | | | |
| A | Baseline | S | S | S | S | S | S | S | S | S | S |
| B1 | Baseline | I | S | I | D | I+ | I | I | S | I | I |
| B2 | Baseline | S | I | I | D | I | I+ | S | I | I | I |
| B3 | Baseline | I | I | I | D | I+ | I+ | I | I | I | I |
| C1 | Baseline | I | S | D | I | I | S | I+ | I | I | I |
| C2 | Baseline | S | I | D | I | S | I | I | I+ | I | I |
| C3 | Baseline | I | I | D | I | I | I | I+ | I+ | I | I |
| D1 | Baseline | S | I | S | S | S | I | S | I | I | I |
| D2 | Baseline | I | S | S | S | I | S | I | S | I | I |
| E1 | Baseline | I | I | I | I | I+ | I+ | I+ | I+ | I | S |
| E2 | Baseline | I | I | I | I | I+ | I+ | I+ | I+ | S | I |
| F1 | Baseline | I | I | I | I | I+ | I+ | I+ | I+ | I | I |
| F2 | Baseline | I | I | I | I | I+ | I+ | I+ | I+ | I | I |
| F3 | Baseline | I | I | I | I | I+ | I+ | I+ | I+ | I | I |
| F4 | Baseline | I | I | I | I | I+ | I+ | I+ | I+ | I | I |
| G | Baseline | I | I | I | I | I+ | I+ | I+ | I+ | I | I |

Table 2A, column 1 lists the sixteen possible siderail configurations of Table 1. The row below the column number headings shows the occupant displacements of FIG. 11. Column 2 corresponds to a centered occupant, i.e. displacement=0, as in table 1. The displacements of columns 3-6 are referred to as unidirectional displacements because they involve occupant displacement in only one direction, (left, right, headwardly (up) and footwardly (low)) relative to the centered or reference location. The displacements of columns 7-10 are referred to as bidirectional or composite displacements because they involve occupant displacement in two directions (up and left, up and right, low and left, and low and right) relative to the centered or reference location.

configuration is B3 (both upper siderails DOWN; both lower siderails UP) and the occupant is off center to the left (col. 3), the risk is increased relative to the baseline risk of table 1 because the occupant is displaced to the left, and a left siderail is DOWN. Hence the "I" entry at cell (B3,3). This increase in risk occurs whether the baseline risk of table 1 is considered to be nonzero when at least one siderail is down, even for a centered occupant (as in the example of table 1), or is taken to be zero for a centered occupant irrespective of the siderail configuration.

In another example, if the siderail configuration is C2 (lower right siderail DOWN; the others UP) and the occupant is off center headwardly (up) (col. 5), the risk is decreased relative to the baseline risk of Table 1 because the occupant is displaced headwardly, and the only siderail having a status of DOWN is more footwardly. In other words the occupant is displaced away from a location of risk. Hence the entry "D" at cell (C2, 5).

In another example if the siderail configuration is D2 (both left siderails DOWN; both right siderails UP) and the occupant is off center footwardly (down) (col. 6), the risk is the same as the baseline risk of table 1 because with both left siderails DOWN, occupant displacement toward the foot of the bed is judged to have no influence on risk of exit. Hence the entry "S" at cell (D2, 6).

calculations are given in columns 7-10 of Table 2.1A. These results have been reformatted as I+, I, S, and D entries in columns 7-10 of Table 2A. The "S" entries in Table 2A columns 7-10 correspond to values of 0 in table 2.1A. The "I" entries in Table 2A columns 7-10 correspond to values of 1 in table 2.1A. The "I+" entries in Table 2A columns 7-10 correspond to values of 2 in table 2.1A in order to reflect a risk higher than "I". Alternatively, the designer could choose to not differentiate between values of 1 and 2 in table 2.1A when populating the composite cells of Table 2A and simply indicate an increased risk, "I", rather than gradations of risk "I" and "I+".

TABLE 2.1A

Substitution of 1 for I of table 2A columns 3-6 and 0 for S and D of table 2A columns 3-6 and Calculation of Composite Risks (Columns 7-10). Bidirectional Risks Reflect No Credit for Decreased Unidirectional Risk

| 1 S/R Config | 2 Center | 3 Off center Left | 4 Off center Right | 5 off center Up | 6 Off center Down | 7 Up/Left (col's 3 + 5) | 8 Up/Right (col's 4 + 5) | 9 Low/Left (col's 3 + 6) | 10 Low/Right (col's 4 + 6) |
|---|---|---|---|---|---|---|---|---|---|
| | | | | Weight Distribution | | | | | |
| A | Baseline | 0 | 0 | 0 | 0 | 0 | 0 | 0 | 0 |
| B1 | Baseline | 1 | 0 | 1 | 0 | 2 | 1 | 1 | 0 |
| B2 | Baseline | 0 | 1 | 1 | 0 | 1 | 2 | 0 | 1 |
| B3 | Baseline | 1 | 1 | 1 | 0 | 2 | 2 | 1 | 1 |
| C1 | Baseline | 1 | 0 | 0 | 1 | 1 | 0 | 2 | 1 |
| C2 | Baseline | 0 | 1 | 0 | 1 | 0 | 1 | 1 | 2 |
| C3 | Baseline | 1 | 1 | 0 | 1 | 1 | 1 | 2 | 2 |
| D1 | Baseline | 0 | 1 | 0 | 0 | 0 | 1 | 0 | 1 |
| D2 | Baseline | 1 | 0 | 0 | 0 | 1 | 0 | 1 | 0 |
| E1 | Baseline | 1 | 1 | 1 | 1 | 2 | 2 | 2 | 2 |
| E2 | Baseline | 1 | 1 | 1 | 1 | 2 | 2 | 2 | 2 |
| F1 | Baseline | 1 | 1 | 1 | 1 | 2 | 2 | 2 | 2 |
| F2 | Baseline | 1 | 1 | 1 | 1 | 2 | 2 | 2 | 2 |
| F3 | Baseline | 1 | 1 | 1 | 1 | 2 | 2 | 2 | 2 |
| F4 | Baseline | 1 | 1 | 1 | 1 | 2 | 2 | 2 | 2 |
| G | Baseline | 1 | 1 | 1 | 1 | 2 | 2 | 2 | 2 |

The entries for the bidirectional or composite displacements of columns 7-10, like those of columns 3-6, may be reasoned out logically, or may be derived from the unidirectional entries of columns 3-6. In one example of deriving the entries for the composite displacements (columns 7-10), the entries for the unidirectional displacements (columns 3-6) are each replaced by a numerical value, namely "I" is replaced by 1; D and S are replaced by 0. The entry in each composite cell is computed as the sum of the numerical entries in the appropriate unidirectional cells. For example:

$(B1,7)=(B1,3)+(B1,5)$ i.e. up/left=up+left;

$(B1,8)=(B1,4)+(B1,5)$ i.e. up/right=up+right;

$(B1,9)=(B1,3)+(B1,6)$ i.e. low/left=low+left;

$(B1,10)=(B1,4)+(B1,6)$ i.e. low/right=low+right, and so forth. The numerical results of substituting 1 for the "I" values of Table 2A columns 3-6 and 0 for the "D" and "S" values of Table 2A columns 3-6 are given in columns 3-6 of Table 2.1A, below. The results of the above described Because the foregoing example substitites a value of zero in columns 3-6 of table 2.1A for a both an unchanged unidirectional risk and for a decreased unidirectional risk of table 2A, the composite risk (columns 7-10) increases if either of the unidirectional risks increases, even if one of the unidirectional risks decreases. In other words the foregoing does not recognize any "credit" for a decreased unidirectional risk when deriving the composite risks. In an alternative method, the calculation of the composite risks may reflect the possibility that a decrease in one of the unidirectional risks that contribute to a given composite risk might offset an increase in the other unidirectional risk that contributes to the same composite risk. This is illustrated in Table 2.1B, below, where the affected entries (relative to the entries of table 2.1A) are indicated by a larger and bolder font. The entries in Table 2.1B are the same as those of table 2.1A except for the numerical substitutions at unidirectional cells (B1,6), (B2,6), (B3,6), (C1,5), (C2,5), and (C3,5) These changes affect the results in composite cells (B1, 9), (B1, 10), (B2, 9), (B2, 10), (B3, 9), (B3, 10), (C1, 7), (C1, 8), (C2, 7), (C2, 8), (C3, 7), (C3, 8).

TABLE 2.1B

Substitution of 1 for I of table 2A columns 3-6 and 0 for S and D of table 2A
columns 3-6 and Calculation of Composite Risks (Columns 7-10).
Bidirectional Risks Reflect Credit for Decreased Unidirectional Risk

| 1 S/R Config | 2 Centered | 3 Off centered left | 4 Off centered right | 5 off centered up | 6 Off centered down | 7 Up/Left (col's 3+5) | 8 Up/Right (col's 4+5) | 9 Low/Left (col's 3+6) | 10 Low/Right (col's 4+6) |
|---|---|---|---|---|---|---|---|---|---|
| A | Baseline | 0 | 0 | 0 | 0 | 0 | 0 | 0 | 0 |
| B1 | Baseline | 1 | 0 | 1 | -1 | 2 | 1 | 0 | -1 |
| B2 | Baseline | 0 | 1 | 1 | -1 | 1 | 2 | -1 | 0 |
| B3 | Baseline | 1 | 1 | 1 | -1 | 2 | 2 | 0 | 0 |
| C1 | Baseline | 1 | 0 | -1 | 1 | 0 | -1 | 2 | 1 |
| C2 | Baseline | 0 | 1 | -1 | 1 | -1 | 0 | 1 | 2 |
| C3 | Baseline | 1 | 1 | -1 | 1 | 0 | 0 | 2 | 2 |
| D1 | Baseline | 0 | 1 | 0 | 0 | 0 | 1 | 0 | 1 |
| D2 | Baseline | 1 | 0 | 0 | 0 | 1 | 0 | 1 | 0 |
| E1 | Baseline | 1 | 1 | 1 | 1 | 2 | 2 | 2 | 2 |
| E2 | Baseline | 1 | 1 | 1 | 1 | 2 | 2 | 2 | 2 |
| F1 | Baseline | 1 | 1 | 1 | 1 | 2 | 2 | 2 | 2 |
| F2 | Baseline | 1 | 1 | 1 | 1 | 2 | 2 | 2 | 2 |
| F3 | Baseline | 1 | 1 | 1 | 1 | 2 | 2 | 2 | 2 |
| F4 | Baseline | 1 | 1 | 1 | 1 | 2 | 2 | 2 | 2 |
| G | Baseline | 1 | 1 | 1 | 1 | 2 | 2 | 2 | 2 |

Table 2B, below is the same as Table 2A except that the entries in Table 2B are based on those of table 2.1B and therefore take advantage of the "credits" of Table 2.1B thus reflecting a presumed decrease in risk for occupant displacement in a direction away from a DOWN siderail. The entries in cells cells (B1, 9), (B1, 10), (B2, 9), (B2, 10), (B3, 9), (B3, 10), (C1, 7), (C1, 8), (C2,7), (C2, 8), (C3, 7), and (C3, 8) of table 2B differ from the corresponding entries in Table 2A to reflect the "credit". The "D" entries in table 2B correspond to values of −1 in table 2.1B. The "S" entries in table 2B correspond to values of 0 in table 2.1B. The "I" entries in Table 2B correspond to values of 1 in table 2.1B. The "I+" entries in Table 2B correspond to values of 2 in table 2.1B in order to reflect a risk higher than "I". Alternatively, the designer could choose to not differentiate between values of 1 and 2 when populating the composite cells of Table 2B and simply indicate an increased risk, "I", rather than gradations of risk "I" and "I+".

TABLE 2B

Risk Adjustment Due to Occupant Displacement from Reference Location (With
Credit in the Composite Risks for Decreased Unidirectional Risk)

| 1 S/R Config | 2 Center | 3 Off center Left | 4 Off center Right | 5 off center Up | 6 Off center Down | 7 Up/Left | 8 Up/Right | 9 Low/Left | 10 Low/Right | 11 diag. UL to LR | 12 diag. UR to LL |
|---|---|---|---|---|---|---|---|---|---|---|---|
|   |   |   | Unidirectional |   |   |   | Composite or Bidirectional |   |   | Diagonal | |
|   |   |   |   | Weight Distribution | | | | | | | |
| A | Baseline | S | S | S | S | S | S | S | S | S | S |
| B1 | Baseline | I | S | I | D | I+ | I | S | D | I | I |
| B2 | Baseline | S | I | I | D | I | I+ | D | S | I | I |
| B3 | Baseline | I | I | I | D | I+ | I+ | S | S | I | I |
| C1 | Baseline | I | S | D | I | S | D | I+ | I | I | I |
| C2 | Baseline | S | I | D | I | D | S | I | I+ | I | I |
| C3 | Baseline | I | I | D | I | S | S | I+ | I+ | I | I |
| D1 | Baseline | S | I | S | S | S | I | S | I | I | I |
| D2 | Baseline | I | S | S | S | I | S | I | S | I | I |
| E1 | Baseline | I | I | I | I | I+ | I+ | I+ | I+ | I | S |
| E2 | Baseline | I | I | I | I | I+ | I+ | I+ | I+ | S | I |
| F1 | Baseline | I | I | I | I | I+ | I+ | I+ | I+ | I | I |
| F2 | Baseline | I | I | I | I | I+ | I+ | I+ | I+ | I | I |
| F3 | Baseline | I | I | I | I | I+ | I+ | I+ | I+ | I | I |
| F4 | Baseline | I | I | I | I | I+ | I+ | I+ | I+ | I | I |
| G | Baseline | I | I | I | I | I+ | I+ | I+ | I+ | I | I |

Referring now to columns 11 and 12 of Tables 2A and 2B, with only two exceptions the risks of the diagonal orientations are all set to I to reflect the fact that the occupant's orientation places either her head or feet in a sector where the siderail is DOWN. The exceptions are siderail configuration E1 for a clockwise displaced occupant and siderail configuration E2 for a counterclockwise displaced occupant. In those cases the occupant's head and feet are in sectors of the bed where the siderail is UP and therefore presents a barrier against occupant exit. Therefore the risk of occupant egress due to her position (orientation) has been judged to be the same as that of a centered occupant.

The foregoing examples (Tables 2A, 2B) show the baseline risk (occupant centered) as increasing (I or I+), decreasing (D) or remaining the same (S) as a function of siderail configuration and occupant displacement. These qualitative, symbolically indicated changes can be quantified. This is demonstrated in the example of table 3A-INCR and table 3A-AGGR. Table 3A-INCR is the same as table 2A except that the entries in columns 3-12 are quantified risk increments corresponding to the symbolic risk adjustments of table 2A. In the example, the quantifications of I+, I, S, and D are +15, +10, 0, and 0 respectively. For example the value of 10 at (C2, 9) of table. 3A-INCR corresponds to the symbol I at cell (C2, 9) of table 2A. In another example the value of 15 at (E1,10) of table 3A-INCR corresponds to the symbol I+ at cell (E1, 10) of table 2A. In these examples the quantifications (I+=15, I=10, S=0, D=0) are not in a linear relationship with the values of table 2.1A (I+=2, I=1, S=0, D=0), however a linear relationship can be used if desired.

TABLE 3A-INCR

Risk Increments Due to Occupant Displacement

| 1 S/R Config | 2 | 3 Off center left | 4 Off center right | 5 off center up | 6 Off center down | 7 up left | 8 up right | 9 low left | 10 low right | 11 diag. UR to LL | 12 diag. UL to LR |
|---|---|---|---|---|---|---|---|---|---|---|---|
|   |   |   |   |   | Weight Distribution |   |   |   |   |   |   |
| A |   | 0 | 0 | 0 | 0 | 0 | 0 | 0 | 0 | 0 | 0 |
| B1 |   | 10 | 0 | 10 | 0 | 15 | 10 | 10 | 0 | 10 | 10 |
| B2 |   | 0 | 10 | 10 | 0 | 10 | 15 | 0 | 10 | 10 | 10 |
| B3 |   | 10 | 10 | 10 | 0 | 15 | 15 | 10 | 10 | 10 | 10 |
| C1 |   | 10 | 0 | 0 | 10 | 10 | 0 | 15 | 10 | 10 | 10 |
| C2 |   | 0 | 10 | 0 | 10 | 0 | 10 | 10 | 15 | 10 | 10 |
| C3 |   | 10 | 10 | 0 | 10 | 10 | 10 | 15 | 15 | 10 | 10 |
| D1 |   | 0 | 10 | 0 | 0 | 0 | 10 | 0 | 10 | 10 | 10 |
| D2 |   | 10 | 0 | 0 | 0 | 10 | 0 | 10 | 0 | 10 | 10 |
| E1 |   | 10 | 10 | 10 | 10 | 15 | 15 | 15 | 15 | 10 | 0 |
| E2 |   | 10 | 10 | 10 | 10 | 15 | 15 | 15 | 15 | 0 | 10 |
| F1 |   | 10 | 10 | 10 | 10 | 15 | 15 | 15 | 15 | 10 | 10 |
| F2 |   | 10 | 10 | 10 | 10 | 15 | 15 | 15 | 15 | 10 | 10 |
| F3 |   | 10 | 10 | 10 | 10 | 15 | 15 | 15 | 15 | 10 | 10 |
| F4 |   | 10 | 10 | 10 | 10 | 15 | 15 | 15 | 15 | 10 | 10 |
| G |   | 10 | 10 | 10 | 10 | 15 | 15 | 15 | 15 | 10 | 10 |

Table 3A-AGGR col. 2 shows the baseline risk of table 1. Columns 3-12 show the aggregate risk for each of the non-centered occupant positions obtained by adding the baseline risk (col. 2) to the the increments of table 3A-INCR. For example the value of 30 in cell (E2,5) of table 3A-AGGR equals the baseline risk of siderail configuration E2 (20) plus an increment (10) for an occupant location of "off-center up" (table 3A-INCR, cell (E2,5).

TABLE 3A-AGGR

Aggregate Risk due to Occupant Displacement as Indicated by Weight Distribution. (Incremental Method)

Weight Distribution

| 1 S/R Config | 2 Centered | 3 Off center left | 4 Off center right | 5 off center up | 6 Off center down | 7 up left | 8 up right | 9 low left | 10 low right | 11 diag. UR to LL | 12 diag. UL to LR |
|---|---|---|---|---|---|---|---|---|---|---|---|
| A | 0 | 0 | 0 | 0 | 0 | 0 | 0 | 0 | 0 | 0 | 0 |
| B1 | 10 | 20 | 10 | 20 | 10 | 25 | 20 | 20 | 10 | 20 | 20 |
| B2 | 10 | 10 | 20 | 20 | 10 | 20 | 25 | 10 | 20 | 20 | 20 |
| B3 | 10 | 20 | 20 | 20 | 10 | 25 | 25 | 20 | 20 | 20 | 20 |
| C1 | 20 | 30 | 20 | 20 | 30 | 30 | 20 | 35 | 30 | 30 | 30 |
| C2 | 20 | 20 | 30 | 20 | 30 | 20 | 30 | 30 | 35 | 30 | 30 |
| C3 | 20 | 30 | 30 | 20 | 30 | 30 | 30 | 35 | 35 | 30 | 30 |
| D1 | 25 | 25 | 35 | 25 | 25 | 25 | 35 | 25 | 35 | 35 | 35 |
| D2 | 25 | 35 | 25 | 25 | 25 | 35 | 25 | 35 | 25 | 35 | 35 |
| E1 | 20 | 30 | 30 | 30 | 30 | 35 | 35 | 35 | 35 | 30 | 20 |
| E2 | 20 | 30 | 30 | 30 | 30 | 35 | 35 | 35 | 35 | 20 | 30 |
| F1 | 30 | 40 | 40 | 40 | 40 | 45 | 45 | 45 | 45 | 40 | 40 |
| F2 | 30 | 40 | 40 | 40 | 40 | 45 | 45 | 45 | 45 | 40 | 40 |
| F3 | 30 | 40 | 40 | 40 | 40 | 45 | 45 | 45 | 45 | 40 | 40 |

TABLE 3A-AGGR-continued

Aggregate Risk due to Occupant Displacement as Indicated by Weight Distribution. (Incremental Method)

| 1 S/R Config | 2 Centered | 3 Off center left | 4 Off center right | 5 off center up | 6 Off center down | 7 up left | 8 up right | 9 low left | 10 low right | 11 diag. UR to LL | 12 diag. UL to LR |
|---|---|---|---|---|---|---|---|---|---|---|---|
| F4 | 30 | 40 | 40 | 40 | 40 | 45 | 45 | 45 | 45 | 40 | 40 |
| G  | 30 | 40 | 40 | 40 | 40 | 45 | 45 | 45 | 45 | 40 | 40 |

In another variant, the quantifications may be based on multipliers which yield an amplification of the baseline risk. This technique is demonstrated in the example of tables 4A-MULT and 4A-AMPL. Table 4A-MULT is the same as table 2A except that the entries in columns 3-12 are risk multipliers corresponding to the symbolic risk adjustments of table 2A. In the example, the multipliers corresponding to I+, I, S, and D are 1.2, 1.1, 1.0, and 1.0 respectively. For example the value of 1.1 at (C2, 9) of table 4A-MULT corresponds to the value I at cell (C2, 9) of table. 2A. In another example the value of 1.2 at (B2, 8) of table 4A-MULT corresponds to the value I+ at cell (B2, 8) of table 2A. As in the case of the risk increments and aggregate quantified risk, the relationship between the values of table 4A-MULT and the values of table 2.1A can be linear or nonlinear.

TABLE 4A-MULT

Risk Multipliers due to Occupant Displacement as Indicated by Weight Distribution

| 1 S/R Config | 2 Centered | 3 Off center left | 4 Off center right | 5 off center up | 6 Off center down | 7 up/ left | 8 up/ right | 9 low/ left | 10 low/ right | 11 diag. UL to LR | 12 diag. UR to LL |
|---|---|---|---|---|---|---|---|---|---|---|---|
| A  | 0  | 1.0 | 1.0 | 1.0 | 1.0 | 1.0 | 1.0 | 1.0 | 1.0 | 1.0 | 1.0 |
| B1 | 10 | 1.1 | 1.0 | 1.1 | 1.0 | 1.2 | 1.1 | 1.1 | 1.0 | 1.1 | 1.1 |
| B2 | 10 | 1.0 | 1.1 | 1.1 | 1.0 | 1.1 | 1.2 | 1.0 | 1.1 | 1.1 | 1.1 |
| B3 | 10 | 1.1 | 1.1 | 1.1 | 1.0 | 1.2 | 1.1 | 1.2 | 1.1 | 1.1 | 1.1 |
| C1 | 20 | 1.1 | 1.0 | 1.0 | 1.1 | 1.1 | 1.0 | 1.2 | 1.1 | 1.1 | 1.1 |
| C2 | 20 | 1.0 | 1.1 | 1.0 | 1.1 | 1.0 | 1.1 | 1.1 | 1.2 | 1.1 | 1.1 |
| C3 | 20 | 1.1 | 1.1 | 1.0 | 1.1 | 1.1 | 1.1 | 1.2 | 1.2 | 1.1 | 1.1 |
| D1 | 25 | 1.0 | 1.1 | 1.0 | 1.0 | 1.0 | 1.1 | 1.0 | 1.1 | 1.1 | 1.1 |
| D2 | 25 | 1.1 | 1.0 | 1.0 | 1.0 | 1.1 | 1.0 | 1.1 | 1.0 | 1.1 | 1.1 |
| E1 | 20 | 1.1 | 1.1 | 1.1 | 1.1 | 1.2 | 1.2 | 1.2 | 1.2 | 1.1 | 1.0 |
| E2 | 20 | 1.1 | 1.1 | 1.1 | 1.1 | 1.2 | 1.2 | 1.2 | 1.2 | 1.0 | 1.1 |
| F1 | 30 | 1.1 | 1.1 | 1.1 | 1.1 | 1.2 | 1.2 | 1.2 | 1.2 | 1.1 | 1.1 |
| F2 | 30 | 1.1 | 1.1 | 1.1 | 1.1 | 1.2 | 1.2 | 1.2 | 1.2 | 1.1 | 1.1 |
| F3 | 30 | 1.1 | 1.1 | 1.1 | 1.1 | 1.2 | 1.2 | 1.2 | 1.2 | 1.1 | 1.1 |
| F4 | 30 | 1.1 | 1.1 | 1.1 | 1.1 | 1.2 | 1.2 | 1.2 | 1.2 | 1.1 | 1.1 |
| G  | 30 | 1.1 | 1.1 | 1.1 | 1.1 | 1.2 | 1.2 | 1.2 | 1.2 | 1.1 | 1.1 |

Table 4A-AMPL col. 2 shows the baseline risk of table 1. Columns 3-12 show the amplified risk for each of the non-centered occupant positions obtained by multiplying the baseline risk (col. 2) by the amplifiers of table 4A-MULT. For example the value of 22 in cell (E2,5) of table 4A-AMPL equals the baseline risk of siderail configurations E2 (20) times the 1.1 multiplier of table 4A-MULT for an occupant location of "off-center up" (table 4A-MULT, cell (E2,5).

TABLE 4A-AMPL

Amplified Risk due to Occupant Displacement as Indicated by Weight Distribution

| 1 S/R Config | 2 Centered | 3 Off center left | 4 Off center right | 5 off center up | 6 Off center down | 7 up left | 8 up right | 9 low left | 10 low right | 11 diag. UR to LL | 12 diag. UL to LR |
|---|---|---|---|---|---|---|---|---|---|---|---|
| A  | 0  | 0  | 0  | 0  | 0  | 0  | 0  | 0  | 0  | 0  | 0  |
| B1 | 10 | 11 | 10 | 11 | 10 | 12 | 11 | 11 | 10 | 11 | 11 |
| B2 | 10 | 10 | 11 | 11 | 10 | 11 | 12 | 10 | 11 | 11 | 11 |

TABLE 4A-AMPL-continued

Amplified Risk due to Occupant Displacement as Indicated by Weight Distribution

| 1 S/R Config | 2 Centered | 3 Off center left | 4 Off center right | 5 off center up | 6 Off center down | 7 up left | 8 up right | 9 low left | 10 low right | 11 diag. UR to LL | 12 diag. UL to LR |
|---|---|---|---|---|---|---|---|---|---|---|---|
| B3 | 10 | 11 | 11 | 11 | 10 | 12 | 12 | 11 | 11 | 11 | 11 |
| C1 | 20 | 22 | 20 | 20 | 22 | 22 | 20 | 24 | 22 | 22 | 22 |
| C2 | 20 | 20 | 22 | 20 | 22 | 20 | 22 | 22 | 24 | 22 | 22 |
| C3 | 20 | 22 | 22 | 20 | 22 | 22 | 22 | 24 | 24 | 22 | 22 |
| D1 | 25 | 25 | 27.5 | 25 | 25 | 25 | 27.5 | 25 | 27.5 | 27.5 | 27.5 |
| D2 | 25 | 27.5 | 25 | 25 | 25 | 27.5 | 25 | 27.5 | 25 | 27.5 | 27.5 |
| E1 | 20 | 22 | 22 | 22 | 22 | 24 | 24 | 24 | 24 | 22 | 20 |
| E2 | 20 | 22 | 22 | 22 | 22 | 24 | 24 | 24 | 24 | 20 | 22 |
| F1 | 30 | 33 | 33 | 33 | 33 | 36 | 36 | 36 | 36 | 33 | 33 |
| F2 | 30 | 33 | 33 | 33 | 33 | 36 | 36 | 36 | 36 | 33 | 33 |
| F3 | 30 | 33 | 33 | 33 | 33 | 36 | 36 | 36 | 36 | 33 | 33 |
| F4 | 30 | 33 | 33 | 33 | 33 | 36 | 36 | 36 | 36 | 33 | 33 |
| G | 30 | 33 | 33 | 33 | 33 | 36 | 36 | 36 | 36 | 33 | 33 |

The foregoing are examples of an incremental method and a multiplicative method of quantifying the values of table 2A. These methods of quantification can also be applied to table 2B.

FIG. 13 is a diagram summarizing the foregoing. Block 170 is the baseline risk for a centered occupant as a function of siderail configuration (e.g. col. 6 of table 1 or col. 2 of table 3A-AGGR or col. 2 of table 4A-MULT). Block 172 is the risk adjustment, such as an increment or factor associated with occupant displacement away from the centered or reference location (col. 3-12 of table 3A-INCR or col. 3-12 of table 4A-MULT). Block 174 combines the risks of blocks 170, 172 into an adjusted risk, i.e. an aggregate or amplified risk as seen in columns 3-12 of table 3A-AGGR or table 4A-AMPL. As a practical matter block 176 communicates the quantified risk to a destination.

In the examples above the combined risk output from block 174 is a summation of the constituent risks as described in connection with tables 3A-INCR and 3A-AGGR or a multiplication of a baseline risk by a multiplier as described in connection with tables 4A-MULT and 4A-AMPL. Other techniques for carrying out the "COMBINE" step of block 174 may also be used. If the system designer chooses to assign a baseline risk of zero to all siderail configurations, block 170 may be dispensed with, in which case block 174 reduces to merely the output of block 172. In addition, the multiplicative method will not apply if the baseline risk is zero for any of the siderail configurations B1 through G.

In the interest of simplicity the only perimeter panels considered in the foregoing examples are the siderails. However the footboard is also a perimeter panel and can be readily included, if desired, by expanding the data tables to account for an UP status and a DOWN status of the footboard.

In the foregoing description the risk contributors are siderail configuration (more generally perimeter panel configuration) and occupant displacement. However as seen starting at block 200 of FIG. 13, additional risk contributors may also be taken into account. The collection of additional contributors illustrated in FIG. 13 and described below is not necessarily exhaustive. Moreover, although the additional contributors are shown in FIG. 13 and are described in connection with the quantified risk of FIG. 13, the concept of accounting for additional contributors is also applicable to the graduated but unquantified risk of FIG. 12.

One example of an additional risk contributor is occupant history (block 200). For example if past experience with an occupant shows that she has a history of unauthorized attempts to exit the bed, an occupant history risk contributor can be included in the determination of risk. The occupant history contributor may also be used if the occupant has a history of falling in addition to or instead of having a history of unauthorized egress attempts. This latter example blends the pure risk of a history of unauthorized egress attempts with the consequences that might ensue (the likelihood that the occupant will fall) if an actual egress were to occur and be accompanied by or be otherwise associated with a fall.

Another example of an additional risk contributor is the local environment (block 204). For example if the bathroom is to the right of the bed, siderail configurations in which a right upper or lower siderail is DOWN might be considered to be riskier that a siderail configuration in which a left upper or lower siderail is DOWN. In another example, the location of any tubes, IV poles or other equipment in the vicinity of the bed can be used as a risk adjuster.

Another example of an additional risk contributor is the general condition of the occupant (block 206). For example an occupant recently finished with surgery may be considered less likely to intentionally exit the bed than an occupant well on the way to recovery. The occupant recently released from surgery would represent a lower risk of intentional exit from the bed; the occupant well on the way to recovery would represent a higher risk.

Another example of an additional risk contributor is the occupant's physiological signs (block 208). For example an occupant whose physiological signs indicate she is sleeping may be considered less likely to intentionally exit the bed than an occupant whose physiological signs indicate she is awake and alert. The sleeping occupant would represent a lower risk of intentional exit from the bed; the awake and alert occupant would represent a higher risk. In another example an occupant whose physiological signs indicate she is agitated may be considered more likely to intentionally exit the bed than an occupant whose physiological signs indicate she is calm.

Yet another possible additional risk contributor is a perimeter panel whose status is UP and which is adjacent to a perimeter panel whose status is DOWN (block 210). As used herein an adjacent perimeter panel is one that is the immediate neighbor of the DOWN perimeter panel as one moves along the perimeter of the bed. This is spelled out explicitly in table 5, below:

TABLE 5

| DOWN perimeter Panel | Adjacent perimeter panel(s) |
| --- | --- |
| upper left | lower left |
| lower left | upper left and footboard |
| footboard | lower left and lower right |
| lower right | footboard and upper right |
| upper right | lower right |

Referring additionally to FIG. 14, The UP status of the adjacent perimeter panel may represent an elevated risk because the occupant can use the UP perimeter panel to support herself while egressing across the opening corresponding to the DOWN perimeter panel. Therefore the presence of the UP panel may make it more inviting to the occupant to attempt an egress. For example table 1 identifies the "D" configurations as riskier than the "C" configurations because the "D" configurations present the occupant with an unrestricted opportunity for exit on one entire side of the bed whereas the C configurations provide an egress opportunity along only part of the side of the bed. However The C configurations provide that egress opportunity at sectors 3 and/or 4, which are natural avenues of egress, and also provide an UP siderail on the same side of the bed. Because the occupant can uses the UP siderail for support, the egress risk of configurations C might be judged by the system designer to be greater than that of configurations D. In general, therefore, a perimeter panel whose status is UP and which is adjacent to a perimeter panel whose status is DOWN may represent an additional risk factor. FIG. 14 shows a logic diagram and truth table reflecting the foregoing.

Figure 15:
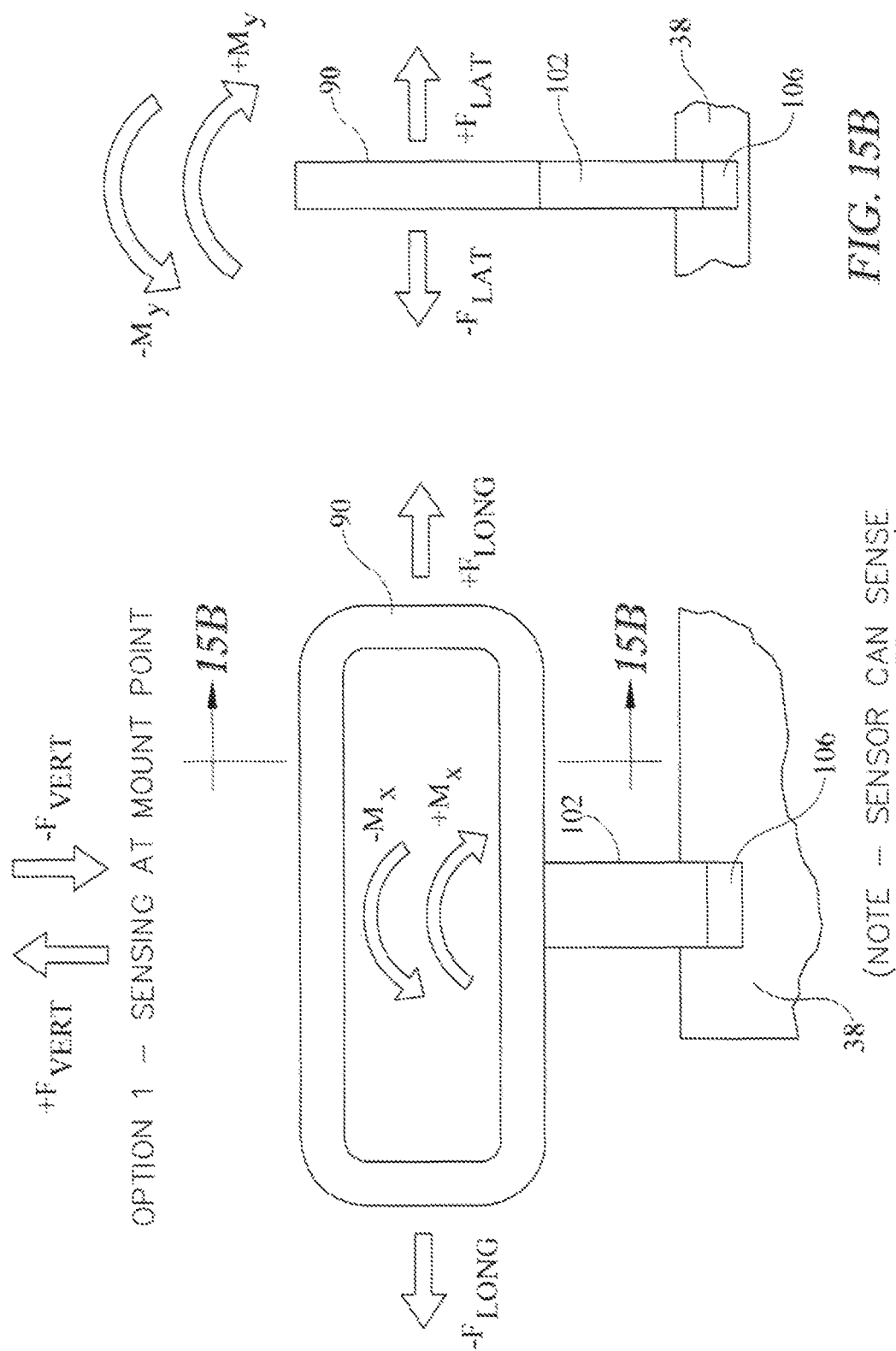
FIGS. 15A and 15B are a schematic side elevation view and a schematic end elevation view of a siderail having a force sensor at the mounting point of the siderail to the frame.
Figure 16:
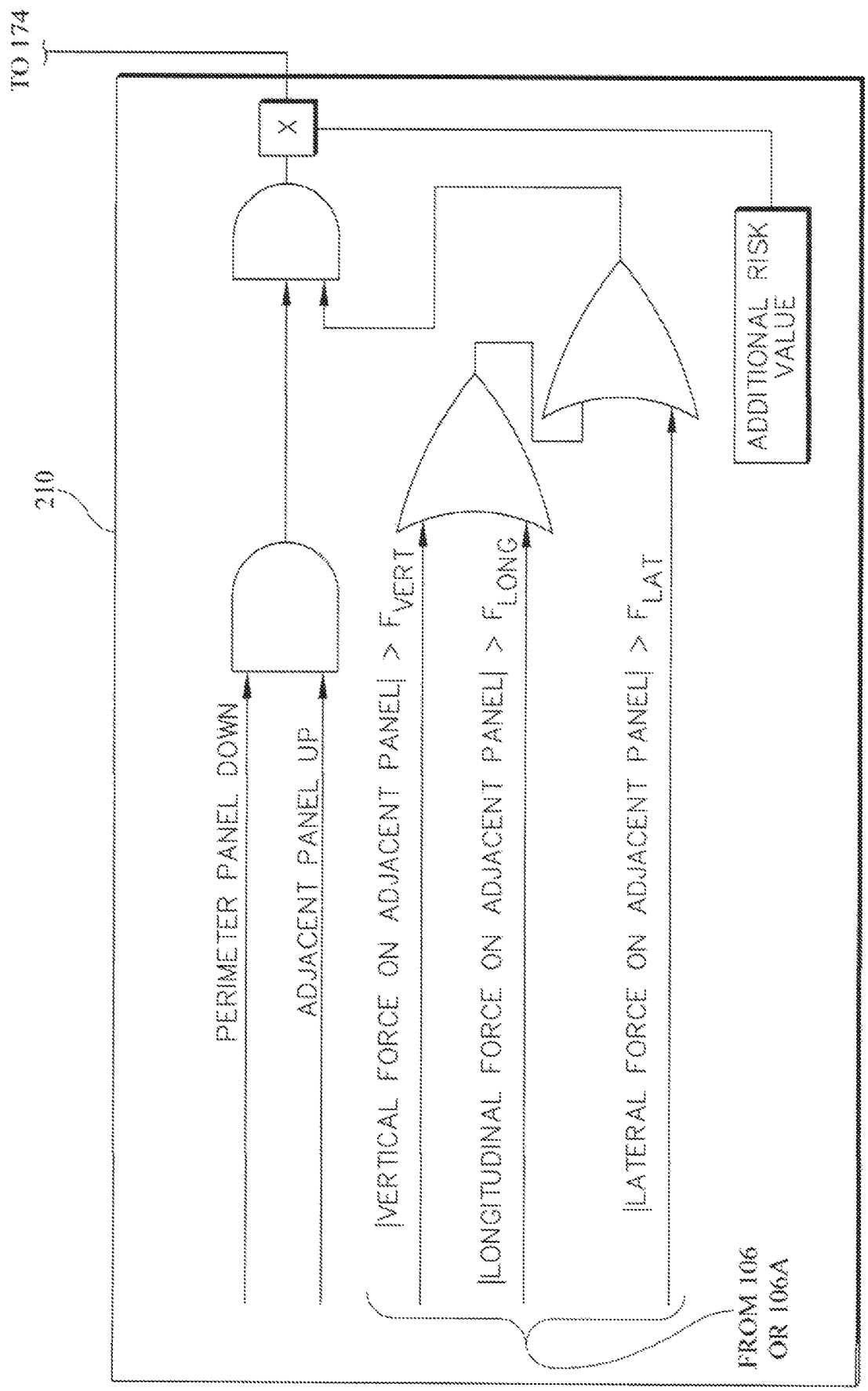
FIG. 16 is a logic diagram showing alternative logic related to the risk contributor described in connection with FIG. 14 and which uses readings from the force sensors of FIGS. 15A and 15B or 17A and 17B.

FIGS. 15A, 15B and 16 disclose a variant on the use of an UP adjacent perimeter panel as an indicator of additional risk. FIG. 15 illustrates a siderail, e.g. upper left siderail 90, a mounting bracket 102 for mounting the siderail to the elevatable frame 38 of the bed, and a force sensor 106. The sensor is positioned at the mounting point of the siderail to the frame and is capable of sensing force in three axes: longitudinally ($\pm F_{LONG}$), laterally ($\pm F_{LAT}$), and vertically ($\pm F_{VERT}$). As seen in the logic diagram of FIG. 16 the additional risk contributor from block 210 is nonzero only if an adjacent perimeter panel is UP and if sensor 106 senses that a force greater than a threshold force is being applied to that UP siderail. The logic diagram considers only the absolute value of the force in each axis and therefore does not distinguish between positively and negatively directed forces. However directional dependency may be incorporated in the direction of one or more of the axes at the discretion of the system designer, in which case the magnitudes of the positive and negative force thresholds need not be equal to each other. In addition, the designer may choose to express the logic in terms of moments M and moment thresholds rather than forces and force thresholds.

Figure 17:
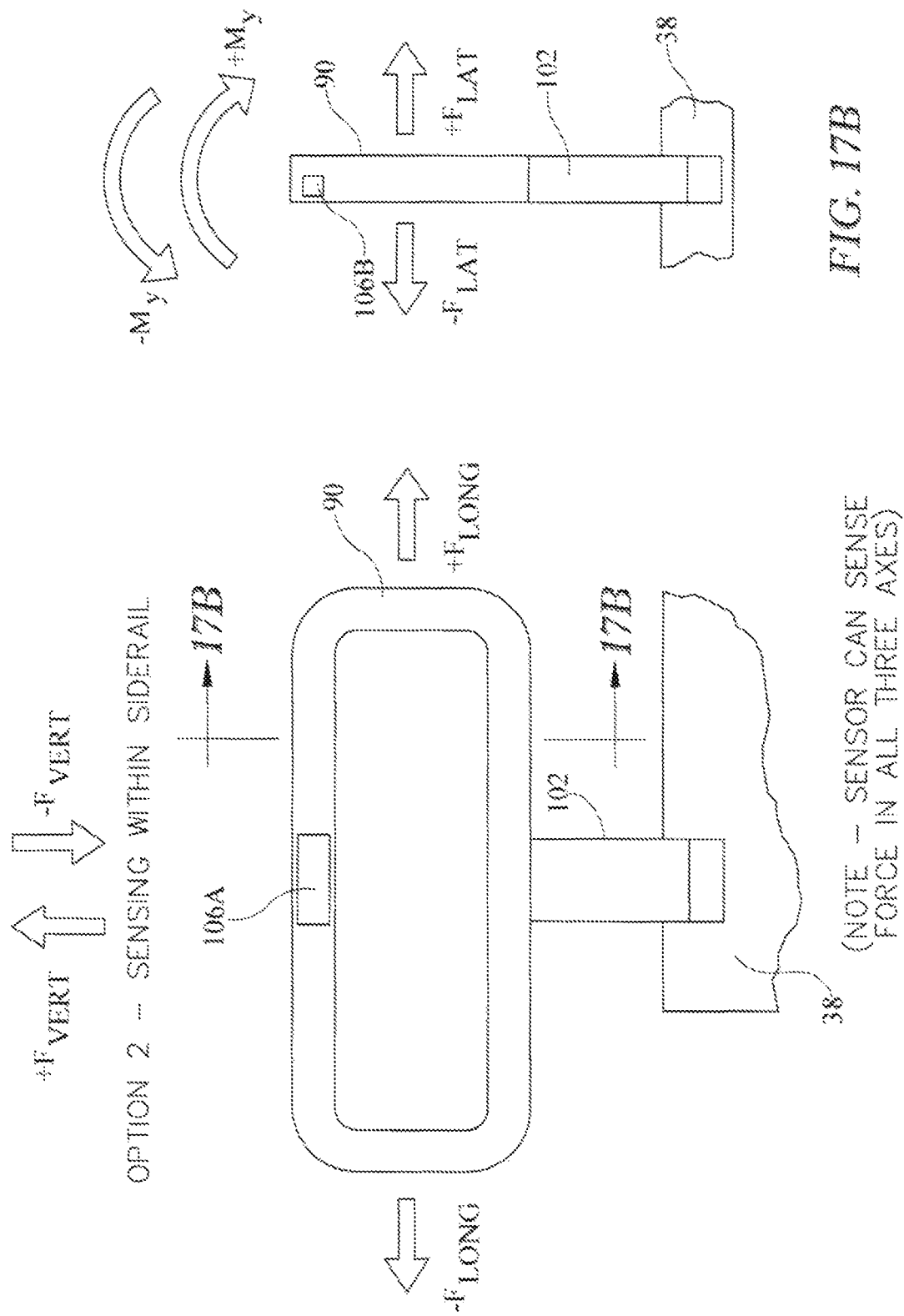
FIGS. 17A and 17B are a schematic side elevation view and a schematic end elevation view of a siderail having a force sensor located in or on the siderail at a point other than the mounting point of the siderail to the elevatable frame.

FIGS. 17A-17B illustrate another variant in which sensor 106, is located in or on the siderail at a point other than the mounting point to the elevatable frame. An acceleraometer is a suitable sensor for the location shown in FIGS. 17A-17B. The logic diagram of FIG. 16 applies to the sensor configuration of FIGS. 17A-17B as well as to that of FIGS. 15A-15B. The variant of FIGS. 17A-17B, like that of FIGS. 15A-15B, may be directionally independent or directionally dependent. The logic may be expressed in terms of forces or in terms of moments.

Referring back to FIG. 13, another additional risk contributor is the state of the bed (block 212) not otherwise accounted for explicitly (as at block 210 which explicitly accounts for the UP or DOWN elevation status of an adjacent perimeter panel) or inherently (as at block 170 which inherently accounts for the UP/DOWN configuration of the siderails). As noted in connection with FIGS. 3-8, many modern hospital beds are elevation adjustable, orientation adjustable, profile adjustable, or some combination thereof. In one specific example of the state of the bed being an additional risk contributor, an occupant may find it awkward to egress from a bed which is in the state shown in FIGS. 7 and 8 ($\theta \neq 0$; $\beta \neq 0$) and therefore may be dissuaded from attempting to egress. In another example an occupant may find it awkward or intimidating to exit from a bed which is in the inclined state of either FIG. 4 or FIG. 5 or is at or near the maximum elevation $E_{MAX}$ of FIG. 3. By contrast, the occupant may find it inviting to exit from a bed which is in the state of FIG. 6, especially if elevation E is not especially high. Accordingly, when the bed is in one of the states of FIG. 4, 5, 7 or 8, or is at or near $E_{MAX}$ of FIG. 3, the overall risk of egress may be adjusted by way of a decrement provided at block 212 and applied at block 174. Similarly, when the bed is in the state shown in FIG. 6, the overall risk of egress may be adjusted by way of an increment provided at block 212 and applied at block 174. The decrement or increment may be a function of E, α, β, θ, and σ.

In another specific example, the designer may conclude that even if egress when the bed is at $E_{MAX}$ is less likely than egress when the bed is at $E_{MIN}$, the possible adverse consequences of egress when the bed is at $E_{MAX}$ justify considering a bed at $E_{MAX}$ to be an in an inherently risker state than if the bed were at $E_{MIN}$. Once again the appropriate adjustment may be applied at block 174 of FIG. 13. This latter example, like that of block 200, blends pure risk of egress with the consequences that would presumably ensue if an actual egress were to occur and be accompanied by or be otherwise associated with an actual adverse event.

Another additional risk contributor is an indication from a second method of assessing the likelihood that the occupant will exit the occupant support (block 214). An example of a second method is the bed exit prediction system described in U.S. Pat. No. 6,208,250 "Patient Position Detection Apparatus for a Bed" to Dixon et. al, (hereinafter Dixon or US '250) the contents of which are incorporated herein by reference, and which is assigned to the assignee of the present application. Briefly, the indications from the exit prediction system of US '250 include 1) an indication that the occupant has moved relative to a reference location on the occupant support apparatus and 2) an indication that the position of the occupant on the occupant support apparatus is suggestive of an intent to exit the apparatus. The algorithms and hardware of the second system and the algorithms and hardware of the system otherwise described herein can be provided as a pre-integrated system. Alternatively, if the second system is a pre-existing system installed on a bed, the algorithms and hardware of the system otherwise described herein can be provided as an upgrade package.

Although the additional risk contributors described above are shown as explicit blocks in FIG. 13, the effects of at least some of them could instead be accounted for in the baseline risk data (e.g. block 170, col. 6 of table 1) or the occupant position risk data (block 172, columns 7-9 of tables 3A-INCR and 4A-MULT) if desired. Of the additional risk contributors described above, the state of the bed (for example as represented by angles β, θ, α, σ) is believed to be suitable for being accounted for in the risk tables, albeit with a concomitant increase in the complexity of the affected table(s). Occupant history and general condition are also believed to be suitable for such treatment, particularly if the occupant history and/or condition can be easily characterized (low, medium or high risk of unauthorized egress/poor, fair or good condition). Moreover, risk contributors described herein as inherently accounted for in the baseline or occupant position risks could be separated out and accounted for as explicit additional risk contributors. In addition, contributors that decrease risk, as well as those that increase risk, can be taken into account.

Some of the additional risk contributors, such as occupant history, local environment, and occupant general condition may be provided on an "as appropriate" basis by a caregiver, for example by providing commands through a keyboard or other input device. Other contributors, such as occupant physiological condition might be better provided automatically from sensors. Other contributors, such as occupant history, may be provided by caregiver input or read from information in an electronic medical record.

Figure 18:
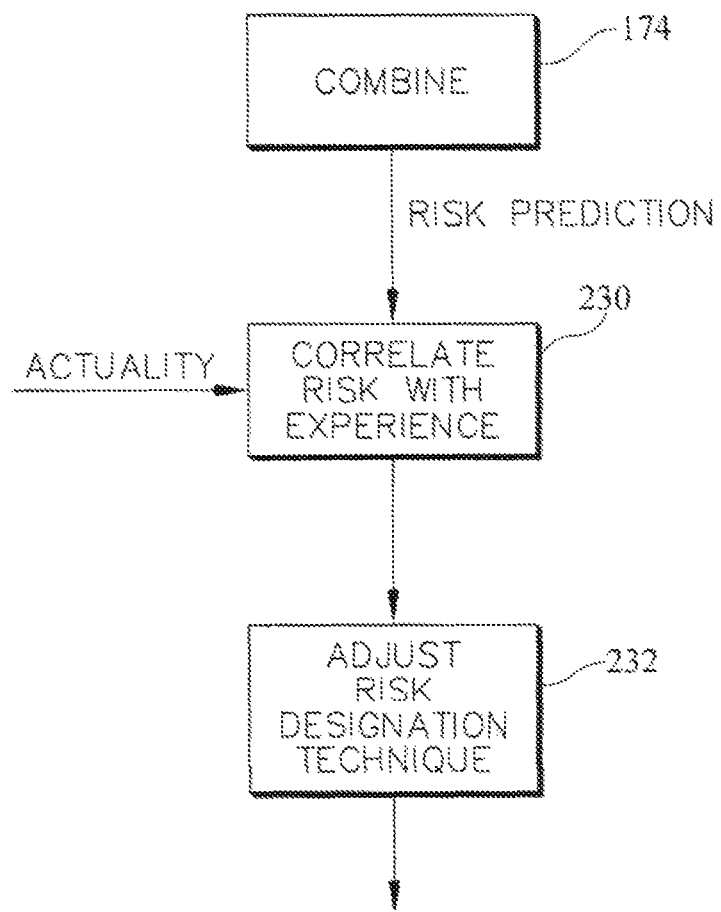
FIG. 18 is a block diagram illustrating the use of a learning algorithm which improves the method of evaluation the risk of egress by correlating a designation of risk with the reality of whether or not an egress actually occurred, and using that correlation to adjust the method.

FIG. 18 is a block diagram illustrating use of a learning algorithm which improves the risk designation by correlating a predicted risk, for example a risk obtained from block 174 of FIG. 13, with the reality of whether or not an egress actually occurred, and using that correlation to update the risk designation method. Block 230 considers the predicted risk of occupant egress derived from a given set of conditions (e.g. perimeter panel configuration, occupant displacement, additional risk contributors) and correlates that predicted risk with the reality of whether or not an egress actually occurred. Block 232 updates the risk prediction technique to cause it to yield, in subsequent predictions, a risk larger or smaller than the risk prediction previously considered at block 230 for the given set of conditions and, optionally, for other sets of conditions considered to be comparable to the given set of conditions. For example the correlation adjusts the prediction algorithm to predict a greater risk if, for a given set of conditions, actual egress occurs at a rate greater than had previously been expected for that set of conditions. Actual egress, or lack of egress, may be detected by an automated system which relies on, for example, pressure sensors on the floor near the bed, or may be a manual system which relies on a user to make an input to a record to indicate whether or not an egress occurred. The adjustment may be a personalized adjustment based on an individual occupant. Alternatively the adjustment may be a "one size fits a class of occupants" adjustment which accounts for the risk prediction and egress reality of a class of occupants (e.g. classes based on occupant gender, height, weight, etc.). In the limit the "one size fits a class" adjustment is a "one size fits all" adjustment applied to all occupants rather than to a class of occupants.

Figure 19:
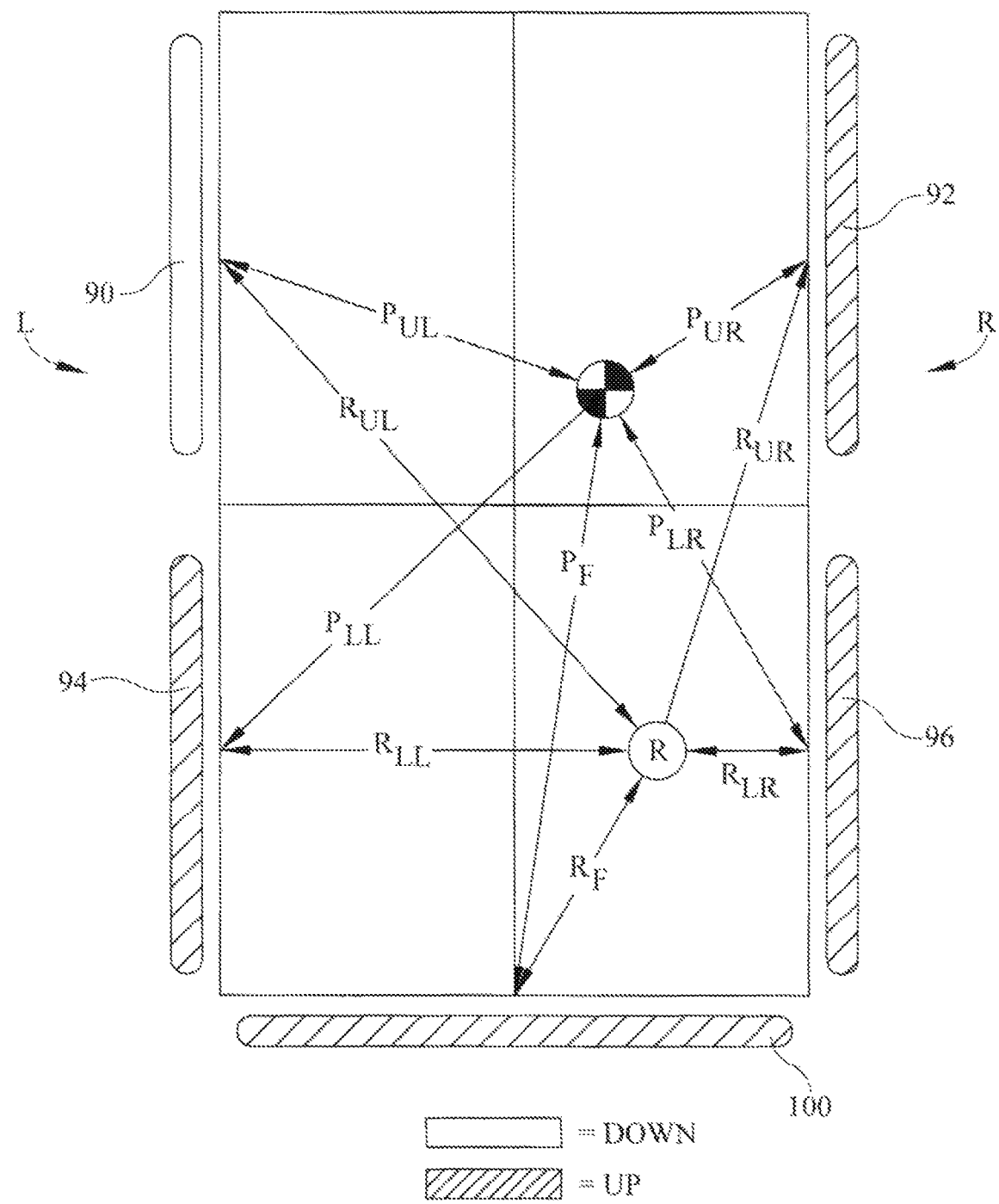
FIG. 19 is a schematic plan view of a bed with five perimeter panels including an upper left siderail having a status of DOWN and also showing an occupant's center of gravity CG and a reference R which does not correspond to the location of a centered occupant.

In the foregoing description the reference location is the location corresponding to a laterally and longitudinally centered occupant. Other reference locations may be chosen if desired. FIG. 19 is a plan view of a bed with five perimeter panels, four siderails and a footboard. Four perimeter panels have a status of UP as indicated by crosshatching. The remaining perimeter panel has a status of DOWN as indicated by the absence of crosshatching. The actual location of the occupant is indicated by the occupant's center of gravity CG which may be estimated from the outputs of force sensors 110. The reference location, which does not correspond to the location of a centered occupant, is indicated by symbol R.

Figure 20:
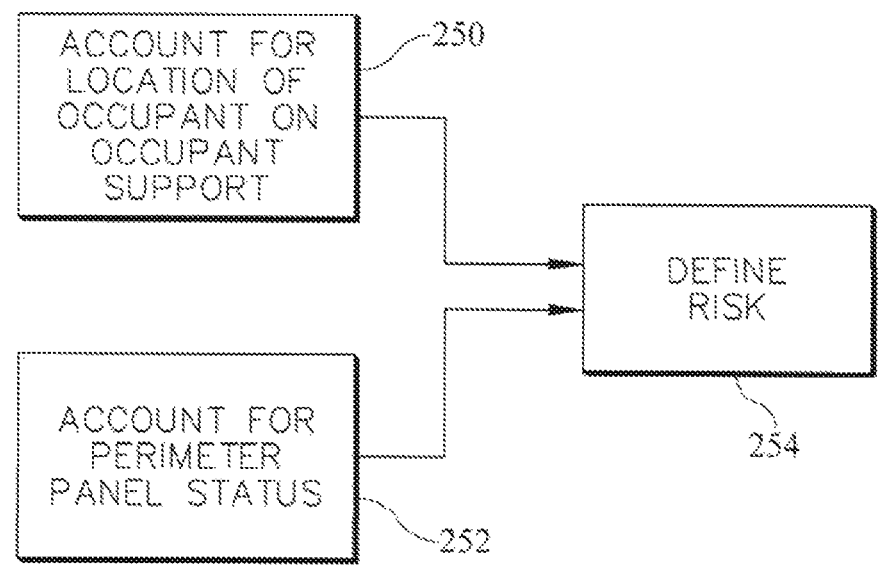
FIG. 20 is a block diagram illustrating a method of evaluating the risk that the occupant whose center of gravity is shown in FIG. 19 will exit the occupant support, the risk according to the method being greater than if the occupant's center of gravity were at the reference location R.

Referring additionally to FIG. 20, with the reference location at a more arbitrary location R, the method of evaluating the risk that the occupant will exit the occupant support, includes a step 250 of accounting for the location of the occupant on the occupant support. As noted above this may be accomplished by using output readings from force sensors 110 to estimate the location of the occupant, for example by estimating the location of the occupant's CG. At block 252 the method accounts for perimeter panel elevation status, in this example UP for a deployed siderail or an installed footboard and DOWN for a stowed siderail or a removed footboard.

At block 254 the method defines the risk of occupant egress as a function of the location of the occupant on the occupant support and the perimeter panel elevation status. One way to define the risk is illustrated with the dimensions $P_i$ and $R_i$ where $P_i$ is the distance from the occupant's CG to the perimeter panel indicated by the subscript ((UL for upper left, UR for upper right, LL for lower left, LR for lower right, and F for footboard) and $R_i$ is the distance from the reference R to the perimeter panel indicated by the subscript.

In one example, the step 250 of accounting for the location of the occupant on the occupant support comprises determining the location of the occupant's CG. The step 252 of accounting for perimeter panel status comprises sensing the status (UP or DOWN) of the perimeter panels. The step 254 of defining the risk comprises comparing the distance $P_i$ to the distance $R_i$ for each perimeter panel whose status is DOWN. If the distance from the occupant to the perimeter panel having a status of DOWN is less than the distance from the reference to the same perimeter panel, the method designates that the occupant is at a greater risk than would be the case if she were at the reference location.

Figure 21:
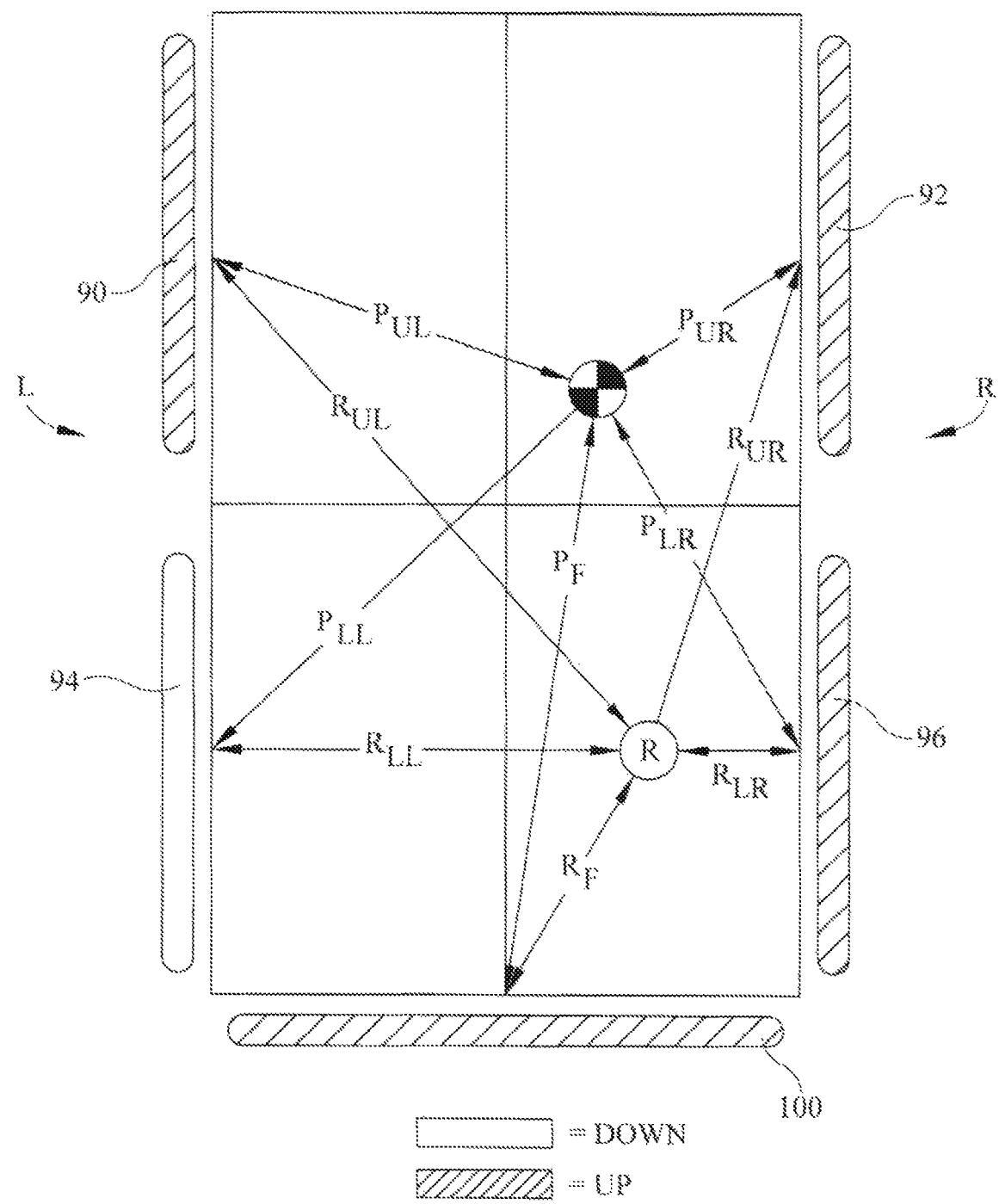
FIG. 21 is a schematic plan view similar to that of FIG. 19 except that the lower left siderail is DOWN so that the method of FIG. 20 designates that the occupant is at less risk of exiting the occupant support than if the occupant's center of gravity were at reference location R.
Figure 22:
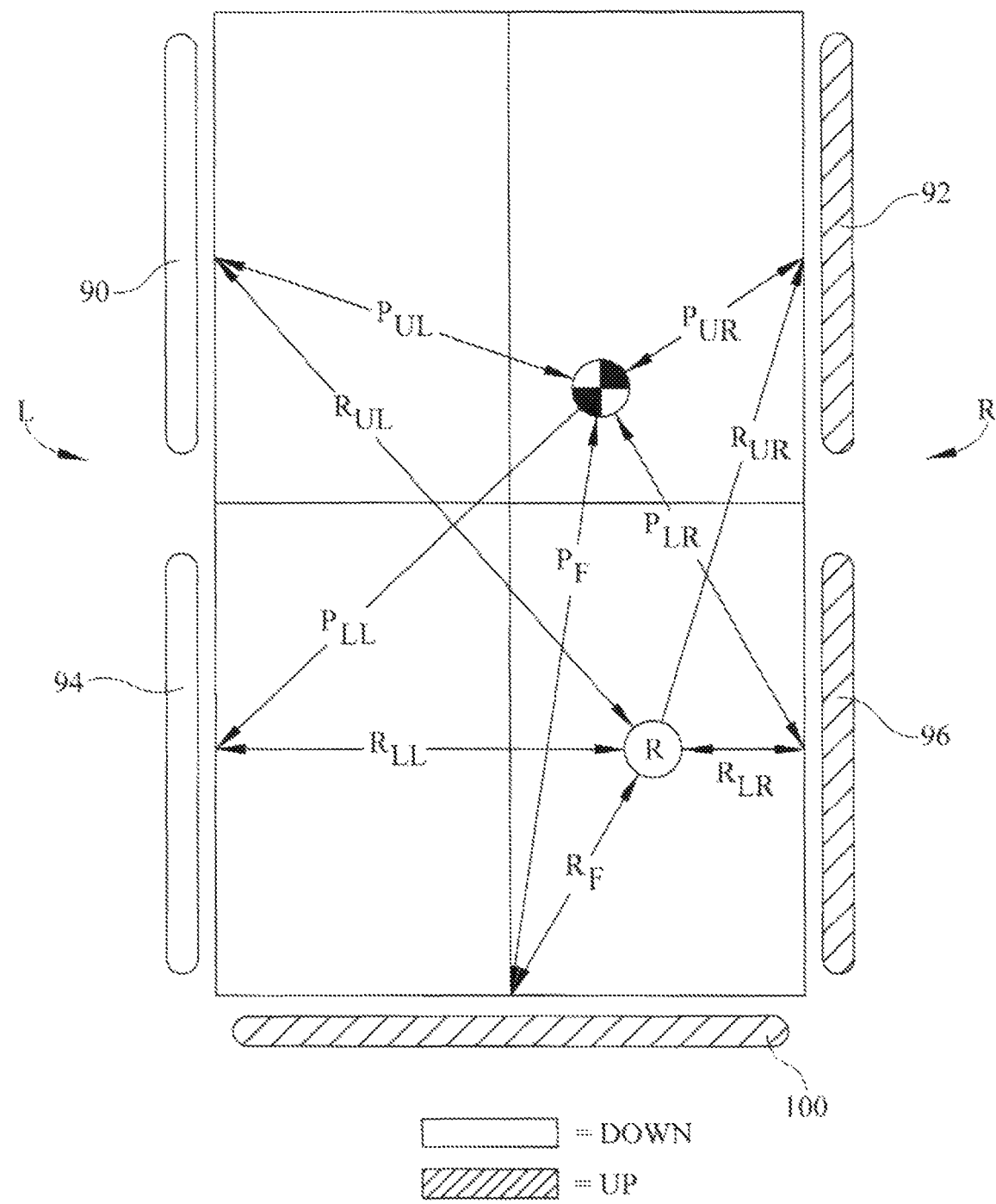
FIG. 22 is a schematic plan view similar to that of FIGS. 19 and 21 except both left siderails are DOWN so that the method of FIG. 20 encounters a dichotomy.

In the specific example of the siderail configuration of FIG. 19, siderail UL is DOWN. Therefore the method compares $P_{UL}$ to $R_{UL}$. Because $P_{UL}$ is less than $R_{UL}$ the occupant is designated as being at greater risk than if her CG were at R. In the specific example of FIG. 21 siderail LL is DOWN. Therefore the method compares $P_{LL}$ to $R_{LL}$. Because $P_{LL}$ is not less than $R_{LL}$ the occupant is designated as being at less risk than if her CG were at R. In the specific example of FIG. 22 siderails UL and LL are both DOWN. Therefore the method compares $P_{UL}$ to $R_{UL}$ and compares $P_{LL}$ to $R_{LL}$. $P_{UL}$ is less than $R_{UL}$ but $P_{LL}$ is not less than $R_{LL}$. The dichotomy may be resolved by specifying that the occupant is at greater risk at her present location than she would be at the reference location if she is at greater risk with respect to even one DOWN siderail. In that case the configuration of FIG. 22 causes the occupant to be at greater risk than if her CG were at the reference location. Of course, even in the case of an arbitrarily selected reference location R as in FIGS. 19, 21, 22, a quantified matrix of siderail configurations and occupant positions can be developed.

Although this disclosure refers to specific embodiments, it will be understood by those skilled in the art that various changes in form and detail may be made without departing from the subject matter set forth in the accompanying claims.

We claim:

1. A support apparatus comprising:
   a framework having perimeter panels, the panels having an elevation status;
   a mattress;
   sensors distributed on the support apparatus to sense occupant weight distribution on the support apparatus; and
   a processor adapted to determine occupant weight distribution relative to a reference weight distribution and to designate a risk of occupant egress as a function of:
   a) occupant weight distribution, and b) whether or not a second perimeter panel, which is adjacent to a first perimeter panel having an elevation status of DOWN, has an elevation status of UP, wherein the designation of risk also takes into account whether or not a force which is greater than a threshold force is acting on the second perimeter panel.

* * * * *